US006291507B1

(12) United States Patent
Faull et al.

(10) Patent No.: US 6,291,507 B1
(45) Date of Patent: Sep. 18, 2001

(54) CHEMICAL COMPOUNDS

(75) Inventors: Alan W Faull; Andrew J Barker; Jason G Kettle, all of Macclesfield (GB)

(73) Assignee: Astrazeneca UK Limited, London (GB)

( * ) Notice: Subject to any disclaimer, the term of this patent is extended or adjusted under 35 U.S.C. 154(b) by 0 days.

(21) Appl. No.: 09/626,241

(22) Filed: Jul. 26, 2000

(30) Foreign Application Priority Data

Feb. 17, 1998 (GB) ........ 9803226

(51) Int. Cl.[7] ........ A61K 31/40; C07D 209/02
(52) U.S. Cl. ........ 514/412; 548/243; 548/253; 548/512; 548/514; 548/516
(58) Field of Search ........ 548/516, 243, 548/253, 512, 514; 514/412

(56) References Cited

U.S. PATENT DOCUMENTS

| | | | |
|---|---|---|---|
| 3,557,142 * | 1/1971 | Bell | 548/516 |
| 3,776,923 * | 12/1973 | Remers et al. | 548/516 |
| 3,997,557 | 12/1976 | Helsley et al. . | |
| 4,608,384 | 8/1986 | Wierzbicki et al. | 514/413 |
| 4,721,725 | 1/1988 | Biller et al. . | |
| 4,751,231 | 6/1988 | Halczenko et al. | 514/412 |
| 4,965,369 | 10/1990 | Maetzel et al. | 548/492 |
| 5,081,145 | 1/1992 | Guindon et al. | 514/419 |
| 5,190,968 | 3/1993 | Gillard et al. | 514/419 |
| 5,254,563 | 10/1993 | Huth et al. | 514/292 |
| 5,272,145 | 12/1993 | Prasit et al. | 514/227.8 |
| 5,273,980 | 12/1993 | Frenette et al. | 514/300 |
| 5,288,743 | 2/1994 | Brooks et al. | 514/365 |
| 5,290,798 | 3/1994 | Gillard et al. | 514/361 |
| 5,308,850 | 5/1994 | Gillard et al. | 514/301 |
| 5,389,650 | 2/1995 | Frenette et al. | 514/337 |
| 5,399,699 | 3/1995 | Kolasa et al. | 546/174 |
| 5,482,960 | 1/1996 | Berryman et al. | 514/414 |
| 5,684,032 | 11/1997 | Elliott et al. | 514/414 |
| 5,852,046 | 12/1998 | Lang et al. | 514/419 |

FOREIGN PATENT DOCUMENTS

| | | |
|---|---|---|
| 298 913 A5 | 3/1992 | (DE) . |
| 0 077 209 | 4/1983 | (EP) . |
| 0 114 014 | 7/1984 | (EP) . |
| 0 186 367 | 7/1986 | (EP) . |
| 0 189 690 | 8/1986 | (EP) . |
| 0 419 049 A1 | 3/1991 | (EP) . |
| 0 480 659 A2 | 4/1992 | (EP) . |
| 0 535 923 A1 | 4/1993 | (EP) . |
| 0 535 924 A1 | 4/1993 | (EP) . |
| 0 535 925 A1 | 4/1993 | (EP) . |
| 0 535 926 A1 | 4/1993 | (EP) . |
| 0 639 573 A1 | 2/1995 | (EP) . |
| 0 275 667 | 7/1998 | (EP) . |
| 2 565 981 | 12/1985 | (FR) . |
| WO 86/00896 | 2/1986 | (WO) . |
| WO 93/12780 | 7/1993 | (WO) . |
| WO 93/16069 | 8/1993 | (WO) . |
| WO 93/20078 | 10/1993 | (WO) . |
| WO 93/25546 | 12/1993 | (WO) . |
| WO 94/14434 | 7/1994 | (WO) . |
| WO 96/03377 | 2/1996 | (WO) . |
| WO 96/18393 | 6/1996 | (WO) . |
| WO 96/31492 | 10/1996 | (WO) . |
| WO 96/33171 | 10/1996 | (WO) . |
| WO 96/37467 | 11/1996 | (WO) . |
| WO 96/37469 | 11/1996 | (WO) . |
| WO 97/12613 | 4/1997 | (WO) . |
| WO 97/12615 | 4/1997 | (WO) . |
| WO 97/30704 | 8/1997 | (WO) . |
| WO 97/35572 | 10/1997 | (WO) . |
| WO 98/06703 | 2/1998 | (WO) . |
| WO 99/33800 | 7/1999 | (WO) . |

OTHER PUBLICATIONS

Harrison et al., J. Chem. Soc., Perkin Trans. 1, 1131–1136, 1995.*

Bobošik et al., "Synthesis of N–Phenylsulfonyl Protected Furo[3,2–b]pyrroles", Collect. Czech. Chem. Commun., vol. 59, 1994, pp. 499–205.

Chemical Abstracts, vol. 123, No. 14, Oct. 2, 1995 Columbus, Ohio, US; abstract No. 179521d, Kataoka, Kenichiro et al.: "Homopiperazines as cell migration inhibitors." Xp002081582 see abstract & JP 95 145060 A (TEJIN LTD).

Dandárováet al., "Reference Data", Magnetic Resonance in Chemistry, vol. 28, 1990, pp. 830–831.

(List continued on next page.)

*Primary Examiner*—Fiona T. Powers
(74) *Attorney, Agent, or Firm*—Pillsbury Winthrop LLP

(57) ABSTRACT

A pharmaceutical composition which comprises a compound of formula (I)

(I)

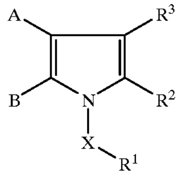

or a pharmaceutically acceptable salt, ester or amide thereof, which is an inhibitor of monocyte chemoattractant protein-1, and wherein A and B form an optionally substituted alkylene chain so as to form a ring with the carbon atoms to which they are attached; X is $CH_2$ or $SO_2$, $R^1$ is an optionally substituted aryl or heteroaryl ring; $R^2$ is a specified organic group such as carboxy, and $R^3$ is hydrogen or a specified organic group; in combination with a pharmaceutically acceptable carrier. Certain compounds of formula (I) are novel and are claimed as such.

17 Claims, No Drawings

OTHER PUBLICATIONS

Database Chemabs, Chemical Abstracts Service, Columbus, Ohio, US, STN, accession No. 125:142551, XP002094570, see abstract. RN 179526–39–7.

Derwent Abstract for JP 63284177 including Chemical Abstract Registry Records for specific compounds indexed.

Derwent World Patents Index record, JAPIO record and Chemical Abstract for Molecules (1997), 2(4), 69–79, including Chemical Abstract Resgistry records for specific compounds indexed.

Hartman et al., "The Synthesis of 5–alkylaminomethylthieno[2,3–b]pyrrole–5–sulfonamides", Heterocycles, vol. 29, 1989, pp. 1943–1949.

Japanese Abstract N–Phenylsulfonylindole derivatives, JP 04273857 A2, 1992.

Krutosikova et al., "Condensed O–, N–Heterocycles by the Transformation of Azidoacrylates", Monatshefte für Chemie 123, 1992, pp. 807–815.

Krutošiková et al., "Derivatives of Furo[3,2–b]pyrrole", Collect. Czech. Chem. Commun., vol. 59, 1994, pp. 473–481.

Krutošiková et al., "Reactions of Methyl 2–Formylfuro[3, 2–b]pyrrole–5–carboxylates", Chem. Papers. vol. 50, 1996, pp. 72–76.

Krutošiková "Subsituted Benzylfuro[3,2–b]pyrroles", Collect. Czech. Chem. Commun., vol. 57, 1992, pp. 1487–1494.

Krutošiková et al., "Substituted Vinyl Azides in Synthesis of Furo[3,2–b:4,5–b]–dipyrroles and Pyrrolo[2',3 3 :4,5]Furo [3,2–c]pyridines", Heterocycles. vol. 37, No. 3, 1994, pp. 1695–1700.

Krutošiková et al., "Substituted Vinyl Azides in the Synthesis of Condensed Nitrogen Heterocycles", Chem. Papers, vol. 48, 1994, pp. 268–273.

Krutošiková et al., "Synthesis and Reactions of Furo[3, 2–b–]pyurrole Type Aldehydes", Czech. Chem. Commun., vol. 58, 1993, pp. 2139–2149.

Murakami et al., "Direct Regioselective Vinylation of Indoles Using Palladium (II) Chloride", Heterocycles, 1984, vol. 22, No. 7, pp. 1493–1496.

Rosenmund et al., "Decarboxylierungen einiger 1–Alkyl–2–carboxy–3–indolessigsäuren sowie Synthese eines 5–Thiocyanato–2,3–dihydroindols", Chemical Berichte, 1975, vol. 108, pp. 3538–3542, XP–00909395.

Troschütz et al., "Synthesis of Substituted 4–Amino–4–cyano–1–oxo–1,2,5,10–tetrahydroazepinol[3, 4–b]indoles", Journal of Heterocyclic Chemistry, Sep.–Oct. 1997, vol. 34, pp. 1431–1440,XP–000909451.

Yokoyama et al., "New Synthetic Method for Dehydrotryptophan Derivatives. Synthetic Studies on Indoles and Related Compounds, XXXIV[1]", Chemical and Pharmaceutical Bulletin, 1994, vol. 42, No. 4, pp. 832–838.

Yokoyama et al.: "Palladium–catalyzed cross–coupling reaction: direct allylation of aryl bromides with allyl acetate" Tetrahedron Letters., vol. 26, No. 52 —1985 pp. 6457–6460, XP002081581 Oxford GB * pp. 6458–6459: compound 7 *.

Harrison, C. A. et al.: "Cyclopenta (b) indoles. Part 2. Model tudies towards the tremorgenic mycotoxins" J. Chem. Soc. Perkin Trans. 1, 1995, pp. 1131–1136, XP002105550 cited in the application, see p. 1132, Scheme 3, compound 9.

Database Chemabs, Chemical Abstracts Service, Columbus, Ohio, US, AN: 119:62465, XP002105556, see abstract & Korobchenko, L. V. et al.: "Sythesis and antiviral activity of pyrrolecarboxylic acids and their derivatives" Khim.–Farm.Zh., vol. 26, No. 11–12, 1992, pp. 57–59, see the whole document.

Berman, J. W. et al.: "Localization of Monocyte Chemoattractant Peptide–I expression in experimental autoimmune encephalomyelitis and trauma in the rat" Journal of Immunology, vol. 156, 1996, pp. 3017–3023, XP002105551 cited in the application, see the whole document.

Jones, M. L. et al.: "Potential role of Monocyte Chemoattractant Protein 1/JE in monocyte/macrophage–dependent IgA immune complex alveolitis in the rat" The Journal of Immunology, vol. 149, No. 6, 1992, pp. 2147–254, XP00210552 cited in the application, see the whole document.

Grimm, M. C. et al.: "Enhanced expression and production of monocyte chemoattractant protein–1 in inflammatory bowel disease mucosa" Journal of Leukocyte Biology, vol.59, No. 6, 1996, pp. 804–12 XP002105555 cited in the application, see the whole document.

Koch, A. E. et al.: "Enhanced production of Monocyte Chemoattractant Protein–1 in rheumatoid arthritis" Journal of Clinical Investigation, vol. 90, No. 3, 1992, pp. 772–779, XP002105553, cited in the application, see the whole document.

Deleuran, M. et al.: "Localization of monocyte chemotactic and activating factor (MCAF/MCP–1) in psoriasis" Journal of Dermatological Science, vol. 12, No. 3, pp. 228–236, XP002105554 cited in the application,see the whole document.

* cited by examiner

CHEMICAL COMPOUNDS

The present invention relates to pharmaceutical compositions which comprise anti-inflammatory and immunomodulatory compounds that act via antagonism of the CCR2 receptor (also known as the MCP-1 receptor), leading inter alia to inhibition of Monocyte Chemoattractant Protein-1 (MCP-1). These compounds contain a bicyclic moiety. The invention further relates to novel compounds for use in the compositions, to processes for their preparation, to intermediates useful in their preparation and to their use as therapeutic agents.

MCP-1 is a member of the chemokine family of pro-inflammatory proteins which mediate leukocyte chemotaxis and activation. MCP-1 is a C—C chemokine which is one of the most potent and selective T-cell and monocyte chemoattractant and activating agents known. MCP-1 has been implicated in the pathophysiology of a large number of inflammatory diseases including rheumatoid arthritis, glomerular nephritis, lung fibrosis, restenosis (International Patent Application WO 94/09128), alveolitis (Jones et al., 1992, *J Immunol.,* 149, 2147) and asthma. Other disease areas where MCP-1 is thought to play a part in their pathology are atherosclerosis (e.g. Koch et al., 1992, *J. Clin. Invest.,* 90, 772–779), psoriasis (Deleuran et al., 1996, *J. Dermatological Science,* 13,. 228–236), delayed-type hypersensitivity reactions of the skin, inflammatory bowel disease (Grimm et al., 1996, *J Leukocyte Biol.,* 59,. 804–812), multiple sclerosis and brain trauma (Berman et al, 1996, *J. Immunol.,* 156,. 3017–3023). A CCR2 antagonist may also be useful to treat stroke, reperfusion injury, ischemia, myocardial infarction and transplant rejection.

MCP-1 acts through the CCR2 receptor. MCP-2 and MCP-3 may also act, at least in part, through this receptor. Therefore in this specification, when reference is made to "inhibition or antagonism of MCP-1" or "MCP-1 mediated effects" this includes inhibition or antagonism of other cytokine mediated effects including MCP-2 and/or MCP-3 mediated effects when those cytokines are acting through the MCP-1 receptor.

J. Chem. Soc. Perkin Trans I (1995) 1131–1136 discloses a number of bicyclic compounds which are intermediates in the production of biologically active indole compounds.

EP-A-189690 discloses that inter alia certain cycloalkanopyrrole derivatives can be useful in treating elevated intraocular pressure, whilst WO 9730704 suggests that related compounds may be used in treating or preventing macular oedema.

The applicants have found that a class of compounds containing a bicyclic moiety are CCR[1] receptor antagonists. In addition, they appear to inhibit RANTES induced chemotaxis. RANTES (Regulated upon Activation, Normal T-cell Expressed and Secreted) is another chemokine from the same family as MCP-1, with a similar biological profile, but acting though the CCR1 receptor. As a result, these compounds can be used to treat disease mediated by these agents, in particular inflammatory disease.

Accordingly the present invention provides a pharmaceutical composition which comprises a compound of formula (I)

(I)

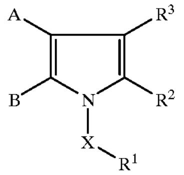

or a pharmaceutically acceptable salt, an ester or amide thereof, which are inhibitors of monocyte chemoattractant protein-l; and wherein A and B form an optionally substituted alkylene chain so as to form a ring with the carbon atoms to which they are attached;

X is $CH_2$ or $SO_2$ $R^1$ is an optionally substituted aryl or heteroaryl ring;

$R^2$ is carboxy, cyano, —$C(O)CH_2OH$, —$CONHR^4$, —$SO_2NHR^5$, tetrazol-5-yl, $SO_3H$, or a group of formula (VI)

(VI)

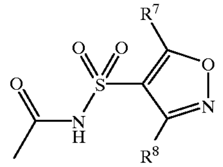

where $R^4$ is selected from hydrogen, alkyl, aryl, cyano, hydroxy, —$SO_2R^9$ where $R^9$ is alkyl, aryl, heteroaryl, or haloalkyl, or $R^4$ is a group-$(CHR^{10})_r$—COOH where r is an integer of 1–3 and each $R^{10}$ group is independently selected from hydrogen or alkyl; $R^5$ is alkyl, optionally substituted aryl such as optionally substituted phenyl or optionally substituted heteroaryl such as 5 or 6 membered heteroaryl groups, or a group $COR^6$ where $R^6$ is hydrogen, alkyl, aryl, heteroaryl or haloalkyl; $R^7$ and $R^1$ are independently selected from hydrogen or alkyl, particularly $C_{1-4}$ alkyl; and $R^3$ is hydrogen, a functional group, optionally substituted alkyl, optionally substituted alkenyl, optionally substituted alkynyl, optionally substituted aryl, optionally substituted heterocyclyl, optionally substituted alkoxy, optionally substituted aralkyl, optionally substituted aralkyloxy, optionally substituted cycloalkyl; in combination with a pharmaceutically acceptable carrier.

Suitably the compositions comprise a compound of formula (I) or a salt or in vivo hydrolysable ester thereof.

Example of such compounds are compounds where A, B, X, $R^1$ and $R^3$ are as defined above, and where $R^2$ is as defined above but that $R^4$ is selected from cyano, hydroxy, —$SO_2R^9$ where $R^9$ is alkyl, aryl, heteroaryl, or haloalkyl, or $R^4$ is a group-$(CHR^{10})_r$—COOH where r is an integer of 1–3 and each $R^{10}$ group is independently selected from hydrogen or alkyl; $R^5$ is optionally substituted phenyl or optionally heteroaryl groups, or a group $COR^6$ where $R^6$ is alkyl, aryl, heteroaryl or haloalkyl; $R^7$ and $R^1$ are independently selected from hydrogen or alkyl, particularly $C_{1-4}$ alkyl.

Compounds of formula (I) are inhibitors of monocyte chemoattractant protein-1 and therefore can be used to treat inflammatory disease. Thus the invention further provides a compound of formula (I) for use in the treatment of inflammatory disease.

In yet a further embodiment, the invention provides the use of a compound of formula (I) in the preparation of a medicament for the treatment of inflammatory disease.

In this specification the term 'alkyl' when used either alone or as a suffix includes straight chained, branched structures. These groups may contain up to 10, preferably up to 6 and more preferably up to 4 carbon atoms. Similarly the terms "alkenyl" and "alkynyl" refer to unsaturated straight or branched structures containing for example from 2 to 10, preferably from 2 to 6 carbon atoms. Cyclic moieties such as cycloalkyl, cycloalkenyl and cycloalkynyl are similar in nature but have at least 3 carbon atoms. Terms such as "alkoxy" comprise alkyl groups as is understood in the art.

The term "halo" includes fluoro, chloro, bromo and iodo. References to aryl groups include aromatic carbocylic groups such as phenyl and naphthyl. The term "heterocyclyl" includes aromatic or non-aromatic rings, for example containing from 4 to 20, suitably from 5 to 8 ring atoms, at least one of which is a heteroatom such as oxygen, sulphur or nitrogen. Examples of such groups include furyl, thienyl, pyrrolyl, pyrrolidinyl, imidazolyl, triazolyl, thiazolyl, tetrazolyl, oxazolyl, isoxazolyl, pyrazolyl, pyridyl, pyrimidinyl, pyrazinyl, pyridazinyl, triazinyl, quinolinyl, isoquinolinyl, quinoxalinyl, benzothiazolyl, benzoxazolyl, benzothienyl or benzofiuryl.

"Heteroaryl" refers to those groups described above which have an aromatic character. The term "aralkyl" refers to aryl substituted alkyl groups such as benzyl.

Other expressions used in the specification include "hydrocarbyl" which refers to any structure comprising carbon and hydrogen atoms. For example, these may be alkyl, alkenyl, alkynyl, aryl, heterocyclyl, alkoxy, aralkyl, cycloalkyl, cycloalkenyl or cycloalkynyl.

The term "functional group" refers to reactive substituents. They may comprise electron-donating or electron-withdrawing. Examples of such groups include halo, cyano, nitro, oxo, $=CR^{11}R^{12}$, $C(O)_nR^{11}$, $OR^{11}$, $S(O)_mR^{11}$, $NR^{12}R^3$, $C(O)NR^{12}R^{13}$, $OC(O)NR^{12}R^{13}$, $=NOR^{11}$, $—CHNOR^{11}$, $—NR^{12}C(O)_nR^{11}$, $—NR^{11}CONR^{12}R^{13}$, $—N=CR^{12}R^{13}$, $S(O)_mNR^{12}R^{13}$ or $—NR^{12}S(O)_mR^{11}$ where $R^{11}$, $R^{12}$ and $R^{13}$ are independently selected from hydrogen or optionally substituted hydrocarbyl, or $R^{12}$ and $R^{13}$ together form an optionally substituted ring which optionally contains further heteroatoms such as $S(O)_m$, oxygen and nitrogen, n is an integer of 1 or 2, m is 0 or an integer of 1–3. It should be understood that functional groups may only be double bonded in conditions where two bonds are available. Thus, $R^3$ may not be oxo or a group $=CR^{11}R^{12}$ or $=NOR^{11}$ for example. Where functional groups comprise $S(O)_mNR^{12}R^{13}$ or $—NR^{12}S(O)_mR^{11}$, m is generally an integer from 1–3. For the avoidance of doubt, where $R^{12}$ and $R^{13}$ together form an optionally substituted ring, the ring will comprise a non-aromatic heterocyclyl group as defined above.

Suitable optional substituents for hydrocarbyl groups $R^{11}$, $R^{12}$ and $R^{13}$ include halo, perhaloalkyl such as trifluoromethyl, mercapto, hydroxy, carboxy, alkoxy, heteroaryloxy, alkenyloxy, alkynyloxy, alkoxyalkoxy, aryloxy (where the aryl group may be substituted by halo, nitro, or hydroxy), cyano, nitro, amino, mono- or di-alkyl amino, oximino (such as hydroxyimino or alkoxyimino) or S(O) mRy where m is as defined above and $R^y$ is alkyl.

Suitably A and B form an alkylene chain which comprises from 3 to 6 carbon atoms so that, together with the carbon atoms to which they are attached, rings of from 5 to 8 atoms result. Suitable substituents for the A-B chain include functional groups as defined above or optionally substituted hydrocarbyl groups or optionally substituted heterocyclic groups. Suitable substituents for these hydrocarbyl or heterocylic groups include those listed above for $R^{11}$, $R^{12}$ and $R^{13}$.

Particular examples of substituents for the A-B chain include oxo; $=NOR^{11}$ where $R^{11}$ is as defined above and in particular an oxime, =NOH; optionally substituted alkyl such as aralkyl, carboxyalkyl or the amide derivative thereof; alkoxy; aryloxy; aralkyloxy; or an amino group which is optionally substituted with alkyl, aryl or aralkyl. A specific functional group which is suitable for the A-B chain is a group of sub-formula (IV).

(IV)

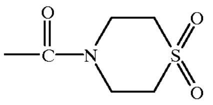

Particular examples of substitutents for the A-B chain are $=NOR^{11}$ groups.

Examples of substitutents which may be found on the A-B ring include carboxy or an alkyl ester thereof, in particular the tert-butyl ester, oxo, =NOH or =NOR* where R* is methyl, benzyl, carboxybenzyl, methoxycarbonylbenzyl, 3-(carboxy)propyl or an ester thereof such as the ethyl ester, 4-carboxybutyl or an ester thereof such as the ethyl ester, and carboxymethyl.

$R^1$ is suitably a single aryl ring.

Suitably $R^1$ is an optionally substituted phenyl, pyridyl, naphthyl, furyl or thienyl ring.

Suitable optional substitutents for $R^1$ in formula (I) include certain of those listed above for $R^{11}$, $R^{12}$ and $R^{13}$ other than aryloxy or heteroaryloxy, as well as alkyl, alkenyl, alkynyl.

Examples of substituents for $R^1$ include trifluoromethyl, $C_{1-4}$alkyl, halo, trifluoromethoxy, $C_{1-4}$alkoxy, $C_{1-4}$alkanoyl, $C_{1-4}$alkanoyloxy, nitro, carboxy, carbamnoyl, $C_{1-4}$alkoxycarbonyl, $C_{1-4}$alkylsulphanyl, $C_{1-4}$alkylsulphinyl, $C_{1-4}$alkylsulphonyl, sulphonamido, carbamoylC, ,alkyl, N-($C_{1-4}$alkyl)carbamoyl$C_{1-4}$alkyl, N-($C_{1-4}$alkyl)$_2$carbamoyl-$C_{1-4}$alkyl, hydroxy$C_{1-4}$alkyl or $C_{1-4}$alkoxy$C_{1-4}$alkyl.

In particular, optional substituents for $R^1$ are selected from halo, haloalkyl including perhaloalkyl such as trifluoromethyl, carboxy, alkoxy, haloalkoxy, alkenyloxy, alkynyloxy, hydroxyalkoxy, alkoxyalkoxy, alkanoyl, alkanoyloxy, cyano, nitro, amino, mono- or di-alkyl amino, sulphonamido or $S(O)_mR^x$ where m is as defined above and $R^x$ is hydrocarbyl. Thus suitable examples are trifluoromethyl, $C_{1-4}$alkyl, halo, trifluoromethoxy, $C_{1-4}$alkoxy, $C_{1-4}$alkanoyl, $C_{1-4}$alkanoyloxy, nitro, carboxy, $C_{1-4}$alkoxycarbonyl, $C_{1-4}$alkylsulphanyl, $C_{1-4}$alkylsulphinyl, $C_{1-4}$alkylsulphonyl, sulphonamido, hydroxy$C_{1-4}$alkyl or $C_{1-4}$alkoxy$C_{1-4}$alkyl.

Additionally or alternatively, two such substituents together may form a divalent radical of the formula $—O(CH_2)_{1-4})—$ attached to adjacent carbon atoms on the $R^1$ ring.

Preferred substitutents for $R^1$ are one or more non-polar substituents such as halo.

In particular, $R^1$ is substituted by one or more halo groups, in particular chlorine. Specific examples of $R^1$ groups are 3,4-dichlorophenyl, 3,4-difluorophenyl, 3-fluoro-4-chlorophenyl, 3-chloro-4-fluorophenyl or 2,3-dichloropyrid-5-yl.

Preferably, $R^1$ is 3,4-dichlorophenyl.

$R^2$ is suitably other than a group $SO_2NH_2$.

Examples of groups $R^2$include carboxy; cyano; tetrazol-5-yl; $SO_3H$; $—CONHR^4$ where $R^4$ is selected from cyano, hydroxy, $—SO_2R^9$ where $R^9$ is alkyl such as $C_{1-4}$ alkyl, aryl such as phenyl, heteroaryl or trifluoromethyl, or $R^4$ is a group-$(CHR^{10})_r$—COOH where r is an integer of 1–3 and each $R^{10}$ group is independently selected from hydrogen or alkyl such as $C_{1-4}$ alkyl; or $R^2$ is a group —$SO_2NHR^5$ where $R^5$ is optionally substituted phenyl or optionally subtituted 5 or 6 membered heteroaryl groups, or a group $COR^6$ where $R^6$ is alkyl such as $C_{1-4}$alkyl, aryl such as phenyl, heteroaryl or trifluoromethyl, or $R^2$ is a group of formula (VI)

(VI)

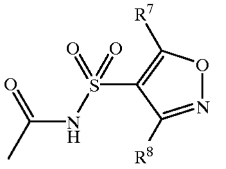

where $R^7$ and $R^1$ arc independently selected from hydrogen or alkyl, particularly $C_{1-4}$alkyl.

Preferably $R^2$ is carboxy or a pharmaceutically acceptable salt or ester thereof, such as a $C_{1-4}$alkyl ester, and particularly carboxy or a pharmaceutically acceptable salt thereof, especially carboxy.

When $R^3$ is an optionally substituted alkyl, alkenyl or alkynyl group, or $R^3$ is a group which includes an alkyl moiety, suitable optional substitutents include halo, perhaloalkyl such as trifluoromethyl, mercapto, hydroxy, carboxy, alkoxy, heteroaryloxy, alkenyloxy, alkynyloxy, alkoxyalkoxy, aryloxy (where the aryl group may be substituted by halo, nitro, or hydroxy), cyano, nitro, amino, mono- or di-alkyl amino, oximino (for example hydroxyimino or alkoxyimino) or $S(O)_mR^y$ where m is as defined above and $R^y$ is alkyl.

When $R^3$ is an aryl, aralkyl, aryloxy, cycloalkyl or heterocyclyl group, suitable substituents include those as listed above for $R^1$.

Suitable groups $R^3$ include hydrogen, fluoro, chloro, bromo, iodo, methyl, cyano, trifluoromethyl, hydroxymethyl, carboxyalkyl, alkoxyalkyl such as $C_{1-4}$alkoxymethyl, methoxy, benzyloxy, carboxyalkoxy such as carboxymethoxy, methylsulphanyl, methylsulphinyl, methylsulphonyl or carboxy$C_{3-6}$cycloalkyl, —$(CHR^{23})_r$—$N^{24}R^{25}$ (where r is 0–2, preferably 1 or 2, each $R^{23}$ is independently hydrogen or alkyl, in particular $C_{1-4}$alkyl, $R^{24}$ and $R^{25}$ are independently selected from H and $C_{1-4}$alkyl or $R^{24}$ and $R^{25}$ together with the nitrogen to which they are attached form a 5 or 6 membered ring optionally containing one firther heteroatom selected from O, N, S, S(O) or $SO_2$. Suitably $R^{24}$ and $R^{25}$ together form a heterocylic ring such as morpholino or piperazinyl.

Other such groups $R^3$ include optionally substituted aryl groups such as optionally substituted phenyl group. Suitable substituents for phenyl groups $R^3$ include one or more groups selected from chlorine, fluorine, methyl, trifluoromethyl, trifluoromethoxy, amino or formyl.

Although $R^3$ may compnse a range of substituents as listed above, it is preferably hydrogen or a small substituent group such as $C_{1-4}$alkyl in particular methyl, halo or trifluoromethyl, and most preferably hydrogen.

Suitably X is $CH_2$.

A preferred class of compounds of formula (I) are those of formula (III)

(III)

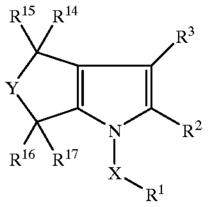

wherein $R^1$, $R^2$, $R^1$ and X are as defined in relation to formula (I), Y is a group $(CR^{18}R^{19})_s$, $R^{14}$, $R^{15}$, $R^{16}$, $R^{17}$and each $R^{18}$ and $R^{19}$ are independently selected from hydrogen, alkyl, cycloalkyl, alkenyl, cycloalkenyl, alkynyl, cycloalkynyl or a functional group, and s is an integer of from 1 to 4. In particular, $R^{14}$, $R^{15}$, $R^{16}$, $R^{17}$ and each $R^{18}$ and $R^{18}$ are independently selected from hydrogen, alkyl, alkenyl, , alkynyl or a functional group Suitable groups for $R^{14}$, $R^{15}$, $R^{16}$, $R^{17}$ and each $R^{18}$ and $R^{19}$ include hydrogen; trifluoromethyl; $C_{1-4}$alkyl which is optionally substituted for example by aryl, carboxy or amide derivatives thereof; halo; hydroxy; $C_{1-4}$alkoxy; $C_{1-4}$alkanoyl; $C_{1-4}$alkanoyloxy; amino; cyano; $C_{1-4}$alkylamino; di($C_{1-4}$alkyl)amino; $C_{1-4}$alkanoylamino; nitro; carbamoyl; $C_{1-4}$alkoxycarbonyl; thiol; $C_{1-4}$alkylsulphanyl; $C_{1-4}$alkylsulphinyl; $C_{1-4}$alkylsulphonyl; sulphonamido; alkylsulphonamnido, arylsulphonarnido, carbamoyl$C_{1-4}$alkyl; N-($C_{1-4}$alkyl)carbamoyl$C_{1-4}$alkyl; N-$(C_{1-4}alkyl)_2$carbamoyl-$C_{1-4}$alkyl; hydroxy$C_{1-4}$alkyl; $C_{1-4}$alkoxy$C_{1-4}$alkyl; morpholino; thiomorpholino; oxythiomorpholino; pyrrolidinyl; carboxy$C_{1-4}$alkylamino; $R^{20}$; $NHR^{21}$ and —$OR^{21}$ where $R^{20}$ and $R^{21}$ are independently selected from optionally substituted phenyl or an optionally substituted 5- or 6-membered heteroaryl ring; or $R^4$ and $R^5$, $R^{16}$ and $R^{17}$, and/or $R^{18}$ and $R^{19}$ together form an oxo group or a group $=NOR^{22}$ where $R^{22}$ is hydrogen or an optionally substituted hydrocarbyl group such as $C_{1-4}$alkyl or aryl substituted with for example a functional group; with the proviso that $R^{14}$ and $R^{15}$, or $R^{16}$ and $R^{17}$ or $R^{18}$ and the $R^{19}$ which is attached to the same carbon atom, are not both hydroxy, $C_{1-4}$alkoxy, amino, cyano, nitro or thiol.

Suitable optional substituents for $R^{20}$ and $R^{21}$ include those listed above for $R^1$.

Examples of such compounds are those where $R^{16}$ and $R^{17}$ are hydrogen.

Further examples include compounds where at least one of $R^{14}$ or $R^{15}$ is other than hydrogen. A preferred example are compounds where $R^{14}$ and $R^{15}$ together form an oxo group. A further preferred example are compounds where $R^{14}$ and $R^{15}$ together form a =NOH or $NOR^{22}$ where $R^{22}$ has a value as defined above for R*.

Yet further examples are compounds where not all of the groups $R^{18}$ and $R^{19}$ are hydrogen, those which are situated close to, for example adjacent to the carbon atom carrying $R^{14}$ and $R^{15}$ are other than hydrogen.

More preferably all of $R^{16}$, $R^{17}$, $R^{18}$ and $R^{19}$ are hydrogen.

Most preferably s is 1 or 2.

A preferred sub-group of compounds of formula (I) are those of formula (III) or a pharmaceutically acceptable salt thereof, where $R^2$ is carboxy or an in vivo hydrolysable ester thereof, X and $R^1$ are as defined above in relation to formula (I), $R^3$ is hydrogen or $C_{1-4}$alkyl, s is as defined in relation to formula (III), $R^{14}$ and $R^{15}$ are selected from hydrogen, =O, =NOH, =NOR* where R* is as defined above, and $R^{16}$, $R^{17}$, $R^{18}$ and $R^{19}$ are all hydrogen.

Suitable pharmaceutically acceptable salts of compounds of formula (I) include acid addition salts such as methanesulfonate, fumarate, hydrochloride, hydrobromide, citrate, maleate and salts formed with phosphoric and sulphuric acid. In another aspect suitable salts are base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine or amino acids for example lysine. There may be more than one cation or anion depending on the number of charged functions and the valency of the cations or anions. A preferred pharmaceutically acceptable salt is a sodium salt.

An in vivo hydrolysable ester of a compound of the formula (I) containing carboxy or hydroxy group is, for example, a pharmaceutically acceptable ester which is hydrolysed in the human or animal body to produce the parent acid or alcohol.

Suitable pharmaceutically acceptable esters for carboxy include alkyl esters, such as $C_{1-4}$alkyl esters for example, ethyl esters, $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

Suitable pharmaceutically acceptable esters of compounds of formula (I) are in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of a-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

Esters which are not in vivo hydrolysable are useful as intermediates in the production of the compounds of formula (I) and therefore these form a further aspect of the invention.

A suitable value for an amide includes, for example, a N-$C_{1-6}$alkyl and N,N-di-($C_{1-6}$alkyl)amide such as N-methyl, N-ethyl, N-propyl, N,N-dimethyl, N-ethyl-N-methyl or N,N-diethylamide.

Examples of compounds of formula (I) are illustrated in Tables I to III below.

TABLE I

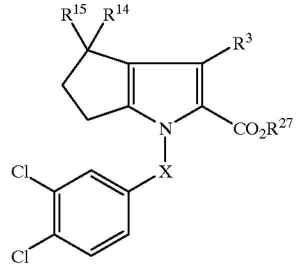

| Compd No. | X | $R^{27}$ | $R^3$ | $R^{14}$ | $R^{15}$ |
|---|---|---|---|---|---|
| 1 | $CH_2$ | $CH_2CH_3$ | H | H | H |
| 2 | $CH_2$ | H | H | H | H |
| 3 | $CH_2$ | $CH_2(C_6H_5)$ | H | $CO_2C(CH_3)_3$ | H |
| 4 | $CH_2$ | $CH_2(C_6H_5)$ | H | $CO_2H$ | H |
| 5 | $CH_2$ | H | H | $CO_2H$ | H |

TABLE II

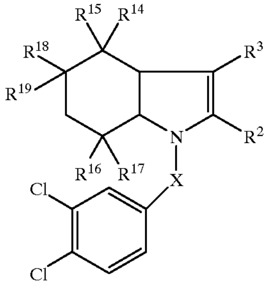

| No. | X | $R^2$ | $R^3$ | $R^{14}$ | $R^{15}$ | $R^{16}$ | $R^{17}$ | $R^{18}$ | $R^{19}$ |
|---|---|---|---|---|---|---|---|---|---|
| 6 | $CH_2$ | $CO_2CH_2CH_3$ | $CH_3$ | | =O | H | H | H | H |
| 7 | $CH_2$ | $CO_2H$ | $CH_3$ | | =O | H | H | H | H |
| 8 | $CH_2$ | $CO_2CH_2CH_3$ | H | H | H | H | H | H | H |
| 9 | $CH_2$ | $CO_2H$ | H | H | H | H | H | H | H |
| 10 | $SO_2$ | $CO_2CH_3$ | H | H | H | H | H | H | H |
| 11 | $SO_2$ | $CO_2H$ | H | H | H | H | H | H | H |
| 12 | $CH_2$ | CN | H | | =O | H | H | H | H |
| 13 | $CH_2$ | $CO_2H$ | H | | =O | H | H | H | H |
| 14 | $CH_2$ | $CO_2CH_2C_6H_5$ | H | | =O | H | H | H | H |
| 15 | $CH_2$ | $CO_2CH_2C_6H_5$ | H | | =O | H | H | CHO | H |
| 16 | $CH_2$ | $CO_2CH_2C_6H_5$ | H | | =O | H | H | | $=N_2$ |

TABLE II-continued

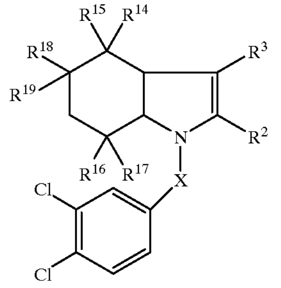

| No. | X | $R^2$ | $R^3$ | $R^{14}$ $R^{15}$ | $R^{16}$ | $R^{17}$ | $R^{18}$ | $R^{19}$ |
|---|---|---|---|---|---|---|---|---|
| 17 | $CH_2$ | $CO_2CH_2CH_3$ | $CH_3$ | $=NOCH_3$ | H | H | H | H |
| 18 | $CH_2$ | $CO_2CH_2CH_3$ | $CH_3$ | $=NOCH_2C_6H_5$ | H | H | H | H |
| 19 | $CH_2$ | $CO_2CH_2CH_3$ | $CH_3$ | $=NOCH_2CO_2H$ | H | H | H | H |
| 20 | $CH_2$ | $CO_2CH_2C_6H_5$ | H | =NOH* | H | H | H | H |
| 21 | $CH_2$ | $CO_2CH_2CH_3$ | $CH_3$ | $=NOH^+$ | H | H | H | H |
| 22 | $CH_2$ | $CO_2CH_2C_6H_5$ | H | $=NOCH_2C_6H_5$▲ | H | H | H | H |
| 23 | $CH_2$ | $CO_2CH_2CH_3$ | $CH_3$ | $=NO(CH_2)_4CO_2CH_2CH_3^+$ | H | H | H | H |
| 24 | $CH_2$ | $CO_2CH_2CH_3$ | $CH_3$ | $=NOCH_2(p-C_6H_5)CO_2CH_3^+$ | H | H | H | H |
| 25 | $CH_2$ | $CO_2CH_2CH_3$ | $CH_3$ | $=NOCH_2(m-C_6H_5)CO_2CH_3^+$ | H | H | H | H |
| 26 | $CH_2$ | $CO_2CH_2CH_3$ | $CH_3$ | $=NO(CH_2)_3CO_2CH_2CH_3^+$ | H | H | H | H |
| 27 | $CH_2$ | $CO_2H$ | $CH_3$ | $=NOCH_3^+$ | H | H | H | H |
| 28 | $CH_2$ | $CO_2H$ | $CH_3$ | $=NOCH_2C_6H_5^+$ | H | H | H | H |
| 29 | $CH_2$ | $CO_2H$ | $CH_3$ | $=NOCH_2CO_2H^+$ | H | H | H | H |
| 30 | $CH_2$ | $CO_2H$ | $CH_3$ | $=NOH^+$ | H | H | H | H |
| 31 | $CH_2$ | $CO_2H$ | H | $=NOCH_2CO_2H^+$ | H | H | H | H |
| 32 | $CH_2$ | $CO_2H$ | H | $=NOCH_2CO_2H$▲ | H | H | H | H |
| 33 | $CH_2$ | $CO_2H$ | H | $=NOCH_2C_6H_5$▲ | H | H | H | H |
| 34 | $CH_2$ | $CO_2H$ | $CH_3$ | $=NOCH_2(m-C_6H_5)CO_2H^+$ | H | H | H | H |
| 35 | $CH_2$ | $CO_2H$ | $CH_3$ | $=NO(CH_2)_3CO_2H^+$ | H | H | H | H |
| 36 | $CH_3$ | $CO_2H$ | $CH_3$ | $=NOCH_2(p-C_6H_5)CO_2H^+$ | H | H | H | H |
| 37 | $CH_2$ | $CO_2H$ | $CH_3$ | $=NO(CH_2)_4CO_2H^+$ | H | H | H | H |

Where *indicates a mixture of isomeric forms
+indicates a Z isomer
▲indicates an E isomer

TABLE III

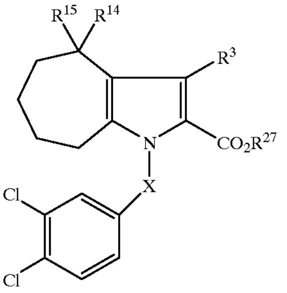

| No. | X | $R^{27}$ | $R^3$ | $R^{14}$ | $R^{15}$ |
|---|---|---|---|---|---|
| 38 | $CH_2$ | $CH_2CH_3$ | $CH_3$ | H | H |
| 39 | $CH_2$ | H | H | H | H |

Certain compounds of formula (I) are novel and these form a further aspect of the invention. Thus the invention further provides a compound of formula (I) as defined above, or a pharmaceutically acceptable salt or in vivo hydrolysable ester thereof, which is an inhibitor of monocyte chemoattractant protein-1; with the proviso that where A and B form $-(CH_2)_3-$, X is $CH_2$, R is carboxy or an ester or amide thereof, and $R^3$ is hydrogen, $R^1$ is other than unsubstituted phenyl.

Particular and preferred groups of novel compounds include those described above in relation to the pharmaceutical compositions.

Some compounds of formula (I) may exist as diastereoisomers and/or may possess chiral centres. It is to be understood that the invention encompasses all such optical isomers and diasteroisomers of compounds of formula (I) and pharmaceutical compositions containing these.

The invention further relates to all tautomeric forms of the compounds of formula (1) and pharmaceutical compositions containing these.

It is also to be understood that certain compounds of the formula (I) can exist in solvated as well as unsolvated forms such as, for example, hydrated forms. It is to be understood that the invention encompasses all such solvated forms and pharmaceutical compositions containing these.

Compounds of formula (I) are suitably prepared by reacting a compound of formula (VII)

VII

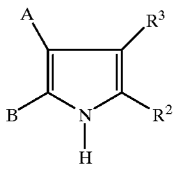

where A, B, $R^2$ and $R^3$ are as defined in relation to formula (I); with compound of formula (VIII)

$R^1$-X-Z VIII where $R^1$ and X are as defined in relation to formula (I) and Z is a leaving group; and optionally thereafter carrying out one or more of the following steps:

(i) converting the group $R^2$ to a different such group:

(ii) introducing or changing a substitutent on the groups A-B:

(iii) converting the group $R^3$ to a different such group.

Suitable leaving groups for Z include halide such as chloride, bromide or iodide, as well as mesylate or tosylate. The reaction is suitably effected in an organic solvent such as dimethylformamide (DMF) tetrahydroflran (THF) or DCM in the presence of a base such as sodium hydride, sodium hydroxide, potassium carbonate. Optionally the reaction is effected in the presence of a suitable phase transfer catalyst. The choice of base and solvent is interdependent to a certain extent in that certain solvents are compatible with some bases only as is understood in the art. For example, sodium hydride may preferably be used with dimethylformamide or tetrahydrofuran and sodium hydroxide is preferably used with dichloromethane and a phase transfer catalyst.

The reaction can be carried out at moderate temperatures, for example from 0 to 50° C. and conveniently at about ambient temperature. Preferably, $R^2$ is an ester group in the compound of formula VII and this may be subsequently converted to an acid or to an amide or to another ester or salt, by conventional methods. For example, when X is a group $SO_2$ and $R^2$ is a methyl ester of carboxy, it may be converted to the corresponding carboxylic acid by reaction with lithium iodide in dry pyridine or DMF.

Compounds of formula (VII) are either known compounds or they may be prepared from known compounds by conventional methods.

For example, compounds of formula (VII) may be prepared by reacting a compound of formula (IX)

(IX)

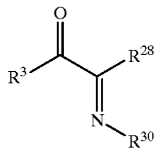

where $R^3$ is as defined in relation to formula (I), $R^{28}$ is a carboxy ester such as an alkyl ester and $R^{30}$ is a group which can be removed under reductive conditions such as —NH ($C_6H_5$); with a cyclic ketone of formula (X)

(X)

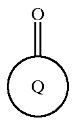

where Q forms a cycloalkyl ring, for example of from 5 to 8 carbon atoms.

The reaction in suitably effected in an organic solvent such as organic acids such as acetic acid and propionic acid in the presence of base such as sodium acetate and a reducing agent such as zinc.

Compounds of formulae (Viii), (IX) and (X) are known compounds or they can be prepared from known compounds by conventional methods.

Alternatively, where A and B in formula (1) form a six membered ring, the compounds may be prepared by hydrogenation of the corresponding aromatic compound, such as an appropriately substituted indole. Such compounds are known in the art or may be obtained by conventional methods. Hydrogenation may be carried out for example in an organic solvent such as acetic acid and in the presence of a catalyst such as platinum.

Substituents on the ring formed by A-B may be introduced either during synthesis as outlined above or using various methods which would be apparent to the skilled person depending upon the nature of the particular substituent to be introduced. Alternatively, one substituent may be changed for a different substituent using conventional chemical methods. For example, an oxo substitutent may be replaced by an $=NOR^7$ group by reaction with an oxime of formula $H_2N—OR^7$. Alternatively, reductive amination will convert the oxo substituent to an amine. Amines may be converted to amides by reaction with for example acid halides. Wittig reactions may be used in order to introduce alkyl or substituted alkyl susbtitutents. Other possibilities would be apparent to the skilled person.

Certain of the intermediates defined herein are novel and are provided as a further feature of the invention.

According to a further aspect of the invention there is provided a compound of the formula (I) as defined herein, or a pharmaceutically acceptable salt or an in vivo hydrolysable ester thereof, for use in a method of treatment of the human or animal body by therapy. In particular, the compounds are used in methods of treatment of inflammatory disease.

According to a further aspect of the present invention there is provided a method for antagonising an MCP-1 mediated effect in a warm blooded animal, such as man, in need of such treatment, which comprises administering to said animal an effective amount of a compound of formula (I), or a pharmaceutically acceptable salt, or an in vivo hydrolysable ester thereof.

The invention also provides a compound of formula (1) as defined herein, or a pharmaceutically acceptable salt, or an in vivo hydrolysable ester thereof, for use as a medicament.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insulation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable Pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal track, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely Powdered form together with one or more suspending agents, such as sodium carboxyrethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example POlYoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided powder containing particles of average diameter of, for example, 30$\mu$ or much less, the powder itself comprising either active ingredient alone or diluted with one or more physiologically acceptable carriers such as lactose. The powder for-insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on Formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula I will naturally vary according to the nature and severity of the conditions, the age and sex of the animal or patient and the route of administration, according to well known principles of medicine. As mentioned above, compounds of the Formula I are useful in treating diseases or medical conditions which are due alone or in part to the effects of farnesylation of rats.

In using a compound of the Formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred.

The invention is further illustrated, but not limited by the following Examples in which the following general procedures were used unless stated otherwise.

N,N-Dimethylfornamide (DMF) was dried over 4 Å molecular sieves. Anhydrous tetrahydrofuran (THF) was obtained from Aldrich SURESEAL™ bottles. Other commercially available reagents and solvents were used without further purification unless otherwise stated. Organic solvent extracts were dried over anhydrous $MgSO_4$. $_1H$, $^{13}C$ and $^9F$ NMR were recorded on Bruker WM200, WM250, WM300 or WM400 instruments using MeSO-$d_6$ with $Me_4Si$ or $CCl_3F$ as internal standard as appropriate, unless otherwise stated. Chemical shifts are in d (ppm) and peak multiplicities are designated as follows: s, singlet; d, doublet; dd, doublet of doublets; t, triplet; dt, doublet of triplets; q, quartet; m, multiplet; br, broad. Mass spectra were recorded on VG 12-12 quadrupole, VG 70-250 SE, VG ZAB 2-SE or a VG modified AEI/Kratos MS9 spectrometers. For TLC analysis, Merck precoated TLC plates (silica gel 60 F254, d=0.25 mm) were used. Flash chromatography was performed on silica (Merck Kieselgel: Art.9385). Melting point determinations were performed on a Kofler block or with a Buichi melting point apparatus and are uncorrected. All temperatures are in degrees Centigrade.

Preparation 1

Ethyl 2,3-dioxo-4,4,4-trifluorobutanoate2-phenylhydrazone

Sodium nitrite (2.57 g) was added portionwise to aniline (3.22 g) in concentrated HCl (6.5 ml) and water 10 ml) at 0° C. over 15 minutes. The resulting solution was added dropwise to ethyl 2,3-dioxo-4,4,4-trifluorobutanoate (6.31 g) and sodium acetate (6 g) in water (30 ml) at 0° C. to precipitate the product as a red solid which was filtered and dried in vacuo (7.15 g, 72%). The crude hydrazone was used without further purification.

Preparation 2

Ethyl 3-methyl-1,4,5,6,7,8-hexahydrocyclohepta[b]pyrrole-2-carboxylate

Ethyl 2,3-dioxobutanoate-2-phenylhydrazone (20.9 g) (T. D; Lash et al., J. Org. Chem. 1992, 57, 4809–4820) in acetic acid (50 ml) was added dropwise to a stirred solution of sodium acetate (10 g), and cycloheptanone (10 g) in acetic acid (100 ml) at 60° C. over 30 minutes. Throughout the addition, small portions of zinc dust (30 g) were added. The reaction was stirred for an additional hour at 80° C., then poured into ice-water (500 g). The resulting solid precipitate was filtered and recrystallised from ethanol to give the product as white needles (2.77 g, 14%), NMR d($CDCl_3$) 1.38 (3H, t), 1.60–1.95 (6H, m), 2.24 (3H, s), 2.48 (2H, t), 2.68 (2H, t), 4.30 (2H, q), 8.70 (111, bs); M/z (+) 222 ($MH^+$), 176.

Preparation 3

Ethyl 3-trifluoromethyl-4,5,6,7-tetrahydroindole-2-carboxylate

The procedure described in preparation 2 was repeated using the appropriate phenylhydrazone and cycloalkanone in order to obtain the title compound in 10% yield, NMR d($CDCl_3$) 1.37 (3H, t), 1.78 (4H, m), 2.63 (4H, m), 4.36 (2H, q), 9.23 (1H, bs); M/z (–) 260 (M-$H^+$).

Preparation 4

Ethyl 4,5,6.7-tetrahydroindole-2-carboxylate

Ethyl indole-2-carboxylate (0.5 g) and platinum (IV) oxide (0.1 g) in acetic acid (20 ml) were stirred under an atmosphere of hydrogen for 16 hours at ambient temperature. The reaction was then filtered through a pad of celite and basified by addition of aqueous sodium hydroxide (2N). The resulting precipitate was filtered and dried in vacuo to give the product as a white solid (0.17 g, 33%), NMR d($CDCl_3$) 1.35 (3H, t), 1.80 (4H, m), 2.50 (2H, t), 2.60 (2H, t), 4.30 (2H, q), 6.65 (1H, d), 8.70 (1H, bs); M/z (+) 194 ($MH^+$).

Preparation 5

Methyl 4,5,6,7-tetrahydroindole-2-carboxylate

The procedure described in Preparation 4 was repeated using the appropriate indole-2-carboxylic ester to give the title compound in 35% yield, NMR d($CDCl_3$) 1.77 (4H, m), 2.50 (2H, m), 2.60 (2H, m), 3.80 (3H, s), 6.65 (1H, m), 8.70 (1H, bs); M/z (+) 180 ($MH^+$).

EXAMPLE 1

Ethyl 1-(3,4-dichlorobenzyl)1,4,5,6-tetrahydrocyclopenta[b]pvrrole-2-carboxylate (Compound 1 in Table I)

Sodium hydride (25 mg, 60%), was added to a solution of ethyl cyclopenta[b]pyrrole-2-carboxylate (96 mg) (T. Aubert et al., J. Chem. Soc. Perkin Trans. 1, 1989, 1369) and the reaction stirred for 30 minutes. 3,4-Dichlorobenzyl bromide (154 mg) was added and stirring continued for a further 2 hours. The reaction was quenched by addition of water and extracted with ether. Combined organic extracts were dried ($MgSO_4$) and concentrated and the residue purified by column chromatography using isohexane-5% ethyl acetate as eluent to give the product as a white crystalline solid (0.15 g, 83%), NMR d(DMSO) 1.18 (3H, t), 2.30 (1H, m), 2.53 (2H, m), 4.10 (2H, q), 5.40 (2H, s), 6.67 (1H, s), 6.92 (1H, dd), 7.25 (1H, s), 7.57 (1H, d); M/z (+) 338 ($M^+$).

EXAMPLE 2

The procedure described in Example 1 was repeated using the appropriate pyrrole and benzyl halide or arylsulfonyl chloride. Thus were obtained the compounds described below.

EXAMPLE 2a

Ethyl 1-(3,4-dichlorobenzyl)-3-methyl-4-oxo-4,5,6,7-tetrahydroindole-2-carboxylate (Compound No.6 in Table II)

This compound was prepared from ethyl 3-methyl-4-oxo-4,5,6,7-tetrahydroindole-2-carboxylate (T. Lash et al., supra.) in 35% yield, NMR d($CDCl_3$) 1.34 (3H, t), 2.12 (2H, m), 2.48 (2H, t), 2.67 (5H, s+t), 4.25 (2H, q), 5.52 (2H, s), 6.79 (1H, dd), 7.07 (1H, s), 7.38 (1H, d); M/z (+) 380 ($M^+$).

EXAMPLE 2b

Ethyl 1-(3,4-dichlorobenzyl)-3-methyl-1,4,5,6,7,8-hexahydrocycloheptal[b]pyrrole-2-carboxylate (Compound No. 38 in Table IX)

This compound was prepared in 30% yield, d($CDCl_3$) 1.28 (3H, t), 1.60 (4H, m), 1.80 (2H, m), 2.27 (3H, s), 2.52 (4H, m), 4.22 (2H, q), 5.55 (2H, s), 6.74 (1H, dd), 7.04 (1H, d), 7.32 (1H, d); M/z (+) 380 ($M^+$), 219.

Deesterification of this compound will yield Compound No. 39 in Table III.

EXAMPLE 2c

Ethyl 1-(3,4-dichlorobenzyl)-4,5,6,7-tetrahydroindole-2carboxylate Compound No.8 in Table II)

This compound was prepared in 63% yield, NMR d($CDCl_3$) 1.25 (3H, t), 1.80 (4H, m), 2.42 (2H, m), 2.50 (2H, m), 4.20 (2H, q), 5.45 (2H, s), 6.80 (1H, m), 6.83 (1H, s), 7.08 (1H, s), 7.35 (1H, d); M/z (+) 352 ($M^+$).

EXAMPLE 2d

Methyl 1-(3,4-dichlorobenzenesulfonyl)-4,5,6,7-tetrahydroindole-2-carboxylate (Compound No10 in Table II)

The compound was prepared in 19% yield, M/z (+) 387 ($M^+$).

EXAMPLE 3

1-(3,4-Dichlorobenzyl)-1,4,5,6-tetrahydrocyclopenta[b]pyrrole-2-carboxylic Acid (Compound No. 2 in Table I)

Sodium hydroxide (3N, 2 ml) was added to a stirred solution of ethyl-(3,4-dichlorobenzyl)cyclopenta[b]pyrrole-2-carboxylate (0.13 g) from Example 1 above in THF (5 ml) and methanol (5 ml). Stirring was continued for 16 hours at ambient temperature, concentrated in vacuo and the residue dissolved in water. Dropwise addition of acetic acid led to precipitation of the product as a white solid which was filtered and dried (70 mg, 59%), NMR d(DMSO) 2.30 (2H, m), 2.55 (4H, m), 5.44 (2H, s), 6.63 (1H, s), 6.96 (1H, dd), 7.28 (1H, d), 7.58 (1H, d); M/z (–) 310 ($M^+$), 308. Analysis for $C_{15}H_{13}Cl_2NO_2$ found C, 57.8%; H, 4.1%; N, 4.4%; theory C, 58.1%; H. 4.2%; N, 4.5%.

EXAMPLE 4

The procedure described in Example 3 was repeated using the appropriate pyrrole-2-carboxylic ester. Thus were obtained the compounds described below.

EXAMPLE 4a 1-(3,4-Dichlorobenzyl)-3-methyl-4-oxo-4,5,6,7-tetrahydroindole-2-carboxylic Acid (Compound No.7 in Table II)

This compound was obtained using the ester of Example 2a in 46% yield, NMR d(DMSO) 1.98 (2H, m), 2.34 (2H, t), 2.50 (3H, s), 2.69 (2H, t), 5.54 (2H, s), 6.87 (1H, dd), 7.30 (1H, d), 7.57 (1H, d); M/Z (–) 352 ($M^+$), 350, 308, 306, 159, 146.

EXAMPLE 4b 1-(3,4-Dichlorobenzyl)-4,5,6,7-tetrahydroindole-2-carboxylic Acid (Compound 9 in Table II)

This compound was obtained from the ester of Example 2c in 72% yield, NMR d(DMSO) 1.65 (4H, m), 2.42 (4H, m), 5.50 (2H, s), 6.65 (1H, s), 6.82 (1H, m), 7.20 (IS, s), 7.55 (1H, d), 11.90 (1H, bs); M/z (–) 324 ($M^+$), 322. Analysis for $C_{16}H_{15}C_{12}NO_2$ found C, 59.1%; H, 4.8%; N, 4.2%; theory C, 59.3%; H, 4.7%; N, 4.3%.

EXAMPLE 5

1-(3,4-Dichlorobenzenesulfonyl)-4,5,6,7-tetrahydroindole-2-carboxylic Acid (Compound 11 in Table 1I)

Ethyl 1-(3,4-dichlorobenzenesulfonyl)-4,5,6,7-tetrahydroindole -2-carboxylate (66 mg) from Example 2d above and lithium iodide (228 mg) were dissolved in pyridine (5 ml) and heated at reflux for 5 hours, cooled, then concentrated in vacuo. The residue was partitioned between 2N HCl and ether. Combined organic extracts were dried ($MgSO_4$), concentrated, and the residue triturated with ether to give the product as a white crystalline solid which was filtered and dried (18 mg, 28%), NMR d(DMSO) 1.65 (4H, m), 2.38 (2H, m), 2.80 (2H, m), 6.70 (1H, s), 7.90 (2H, m), 8.30 (1H, s); M/z (+) 373 (M-$H^+$).

EXAMPLE 6

1-(3,4-dichlorobenzyl)-4-oxo-4,5,6,7-tetrahydroindole-2-carbonitrile (Compound 12 in Table II)

4-Oxo4,5,6,7-tetrahydroindol-2-carbonitrile (5.5 g) (Estep, K. G.; *Synthetic Communications,* 1995, 25, 507–514) in DMF (100 mL) was stirred with 3,4-dichlorobenzyl chloride (5.86 g), potassium iodide (cat.) and potassium carbonate (5.5 g) overnight until reaction was complete. The mixture was poured onto ice and partitioned between water and methylene chloride. The organic phase was washed with brine and dried ($MgSO_4$), and the solvents removed in vacuo, to afford a pale yellow solid. Trituration with ether afforded the title compound as a white solid (8.71 g, 91%), NMR d($CDCl_3$) 2.20 (2H, dt), 2.50 (2H, t), 2.78 (2H, t), 5.20 (2H, s) 6.95 (1H, dd), 7.20 (2H, m), 7.45 (1H, d); M/z (+) 321 ($MH^+$), 319.

EXAMPLE 7

1-(3,4-Dichlorobenzyl)-4-oxo-4,6,7-tetrahydroindole-2-carboxylic acid (Compound 13 in Table II)

1-(3,4-dichlorobenzyl)-4-oxo-4,5,6,7-tetrahydroindole-2-carbonitrile (3.8 g) was heated at reflux in n-butanol (40 mL) over solid sodium hydroxide (12.8 g) for three days. The reaction was neutralised with HCl (conc.) to form a pale precipitate. The precipitate was filtered, washed with water and dried in vacuo to afford the title compound as a pale grey solid (3.38 g, 84%), NMR d(DMSO), 2.00 (2H, dt), 2.35 (2H, t), 2.70 (2H, t), 5.60 (2H, s), 6.90 (1H, dd), 7.10 (1H, s), 7.27 (1H, d), 7.55 (1H, d); M/z (–) 338 ($M^+$), 336.

EXAMPLE 8

Benzyl 1-(3,4-dichlorobenzyl)-4-oxo-4,5,6,7-tetrahydroindole-2-carboxylate (Compound 14 in Table 11)

1-(3,4-Dichlorobenzyl)-4-oxo-4,5,6,7-tetrahydroindole-2-carboxylic acid (1.32 g) and benzyl bromide (0.68 g) was stirred in DMF (10 mL) over potassium carbonate (0.48 g) for 18 hours. The DMF was removed in vacuo and the residue was dissolved in ethyl acetate (50 mL). The organic solution was washed with 2M HCl and dried over $MgSO_4$. The solvents were removed in vacuo to afford the title compound as a pale solid (1.63 g, 97%), NMR d($CDCl_3$) 2.20 (2H, di), 2.50 (2H, t), 2.70 (2H, t), 5.21 (2H, m), 5.55 (2H, s), 6.80 (1H, d), 7.10 (1H,s), 7.35(6H, s), 7.50(1H, s); M/z(+)430, 428 ($M^+$).

EXAMPLE 9

Benzyl 1-(3,4-dichlorobenzyl)-5-formyl-4-oxo-4,5,6,7-tetrahydroindole-2-carboxylate (Compound 15 in Table II)

To benzyl alcohol (1.29 g) in dry THF (20 mL) was added sodium hydride (0.48 g) and the reaction was allowed to stir until evolution of hydrogen ceased. Benzyl 1-(3,4-dichlorobenzyl)-4-oxo-4,5,6,7-tetrahydroindole-2-carboxylate (1.28 g) in THF was added, followed by benzyl formate (1.62 g), and the reaction was stirred for a further 2 hours. Upon completion, the reaction was poured into 2M HCl and extracted with ethyl acetate (2×100 mL). The organic layer was dried ($MgSO_4$) and concentrated in vacuo. Residual benzyl alcohol was distilled from the oil under reduced pressure to afford an orange gum, which was purified by column chromatography using 20% Ethyl acetate: hexane as eluent to give the title compound as a pale white solid (1.15 g, 84%), NMR d($CDCl_3$) 2.60 (2H, t), 2.70 (2H, t), 5.20 (2H, s), 5.55 (2H, s), 6.75 (1H, dd), 7.10 (1H, s) 7.20–7.40 (8H, m); M/z (–) 456 ($M^+$).

EXAMPLE 10

Benzyl 5-diazo-1-(3,4-dichlorobenzyl)-4-oxo-4,5,6,7-tetrahydroindole-2-carboxylate (Compound 16 in Table II)

Triethyl amine (0.36 mL) was added dropwise to a solution of benzyl 1-(3,4-dichlorobenzyl)-5-formyl-4-oxo-4,5,6,7-tetrahydroindole-2-carboxylate (0.5 g) and p-acetamidobenzenesulphonyl azide (305 mg) at room temperature, and stirred for 18 hours to give a brown solution. The solvent was removed in vacuo to afford a brown oil. Purification by column chromatography, using iso-hexane : 20% ethyl acetate as eluent afforded the title compound as a pale yellow solid (0.31 g, 62%), NMR d($CDCl_3$) 2.80 (2H, t), 3.05 (2H, t), 5.13 (2H, s), 5.57 (2H, s), 6.76 (1H, dd), 7.05 (1H, s), 7.20–7.40 (7H, m); M/z (+) 456, 454 ($M^+$).

EXAMPLE 11

Benzyl 4-tert-butoxycarbonyl-1-(3,4-dichlorobenzyl) cyclopenta[b]pyrrole-2-carboxylate (Compound No. 3 in Table I)

Benzyl 5-diazo-1-(3,4-dichlorobenzyl)-4-oxo-4,5,6,7-tetrahydroindole-2-carboxylate (0.3 g) and t-butanol (1 mL) were heated at 180° C. in collidine (10 mL) for 30 minutes, cooled to room temperature, and poured into diethyl ether. The organic layer was washed with 2M HCl (100 mL), dried ($MgSO_4$), and concentrated in vacuo to afford the title compound as an orange oil (0.32 g, 97%), NMR d($CDCl_3$) 1.45 (9H, s), 2.45–2.80 (4H, m), 3.78 (1H, dd), 5.20 (2H, d), 5.40 (2H, d), 6.80 (1H, dd), 6.95 (1H, s), 7.10 (1H, s), 7.30 (6H, m); M/z (+) 502, 500 ($M^+$).

EXAMPLE 12

Benzyl 4-carboxy-1-(3,4-dichlorobenzyl)cyclopenta[b] pyrrole-2-carboxylate (Compound No. 4 in Table I)

Benzyl 4-tert-butoxycarbonyl-1-(3,4dichlorobenzyl) cyclopenta[b]pyrrole-2-carboxylate (0.7 g) was dissolved in methylene chloride (10 mL) and TFA (3 mL) was added. Stirring was continued for 24 hours and the solvents were removed in vacuo to afford a pale oil. The oil slowly solidified on standing to afford the title product (0.61 g, 98%), NMR d(DMSO) 2.40 (4H, m), 3.70 (1H, t), 5.10 (2H, s), 5.40 (2H, AB d), 6.70 (1H, s), 6.90 (1H, d), 7.30 (6H, m), 7.50 (1H, d); M/z (–) 444, 442 (M-$H^+$).

EXAMPLE 13

1-(3,4-Dichlorobenzyl)cyclopenta[b]pyrrole-2,4-dicarboxylic Acid (Compound No. 5 in Table I)

Benzyl 4-carboxy-1-(3,4-dichlorobenzyl)cyclopenta[b] pyrrole-2-carboxylate (0.1 g) was dissolved in ethyl acetate (5 mL). Palladium on carbon (5% Pd, 10 mg) was added and the reaction was exposed to an hydrogen atmosphere (1.1 atm) for 4 hours until reaction was complete. The hydrogen was evacuated and the resulting solution was filtered through Celite to remove catalyst. The reaction was concentrated in vacuo to afford the crude product, which was dissolved in a minimum of 2M NaOH, diluted with water (1 mL), and then precipitated by addition of dilute aqueous HCl. The solid was collected and dried to yield the title product as a pale cream solid (32 mg, 41%), NMR d(DMSO) 2.40 (4H, m), 3.70 (1H, t), 5.40 (2H, AB d), 6.68 (1H, s), 6.95 (1H, dd), 7.15 (1H, s), 7.58 (1H, d); M/z (–) 355, 353 ($MH^+$).

EXAMPLE 14

Ethyl -(3,4-dichlorobenzyl)-3-methyl-4-oxo-4,5,6,7-tetrahydroindole-2-carboolate Z-O--methyl Oxime (Compound 17 in Table II)

Methoxylamine hydrochloride (44 mg) was added to a mixture of ethyl 1-(3,4-dichlorobenzyl)-3-ethyl-4-oxo-4,5,6,7-tetrahydroindole-2-carboxylate (0.15 g) and pyridine (0.2 mL) in ethanol (10 mL) at ambient temperature and the reaction stirred for 18 hours. The reaction was partitioned between 2N hydrochloric acid and ethyl acetate. Combined organic extracts were dried and concentrated to give the product as a clear gum (0.13 g, 80%), NMR d($CDCl_3$) 1.25 (3H, t), 1.86 (2H, m), 2.5 (2H, t), 2.62 (3H, s), 2.7 (2H, t), 3.92 (3H, s), 4.24 (2H, q), 5.48(2H, s) 6.72 (1H, dd), 7.05 (1H, d), 7.32 (1H, d); M/z (+) 409 ($M^+$).

EXAMPLE 15

The procedure described in Example 14 was repeated using the appropriate hydroxylamine and ketone. Thus were obtained the compounds described below.

Ethyl 1-(3,4 dichlorobenzyl)-3-methyl-4-oxo-4,5,6,7-tetrahydroindole-2-carboxylate Z-O-benzyl Oxime (Compound 18 in Table II)

83% yield, NMR d($CDCl_3$) 1.28 (3H, t), 1.85 (2H, m), 2.5 (2H, t), 2.6 (3H, s), 2.75 (2H, t), 4.22 (2H, q), 5.15 (2H s), 5.45 (2H, s), 6.72 (1H, dd), 7.05 (1H, d), 7.28–7.44 (6H, m); M/z (+) 485 ($M^+$).

Ethyl 1-(3,4-dichlorobenzyl)-3-methyl-4-oxo-4,5,6,7-tetrahydroindole-2-carboxylate Z-O-carboxymethyl Oxime (Compound 19 in Table II)

NMR d($CDCl_3$) 1.31 (3H, t), 1.92 (2H, m), 2.54 (2H, t), 2.55 (3H, s), 2.8 (2H, t), 4.25 (2H, q), 4.66 (2H, s), 5.48 (2H, s), 6.74 (1H, dd), 7.05 (1H, d), 7.35 (1H, d); M/z (+) 451 ($M^+$).

Benzyl 1-(3,4-dichlorobenzyl)-4-oxo-4,5,6,7-tetrahydroindole-2-carboxylate E-oxime and benzyl 1-(3,4-dichlorobenzyl)-4-oxo-4,5,6,7-tetrahydroindole-2-carboxylate Z-oxime (Compound 20 in Table II)

22% yield (E-isomer), NMR d($CDCl_3$) 2.0 (2H, m), 2.5 (2H, t), 2.6 (2H, t), 5.24 (2H, s), 5.5 (2H, s), 6.75 (1H, dd), 7.06 (1H, d), 7.35 (6H, m), 7.91 (1H, s); M/z (–) 441 (M-$H^+$), together with 26% yield (Z-isomer), NMR d($CDCl_3$) 1.92 (2H, m), 2.65 (2H, t), 2.74 (2H, t), 5.21 (2H, s), 5.51 (2H, s), 6.75 (1H, dd), 7.05 (1H, d), 7.31 (7H, m), M/z (–) 441 (M-$H^+$).

Ethyl 1-(3,4-dichlorobenzyl) 3methyl-4-oxo-4,5,6,7-tetrahydroindole-2-carboxylate Z-oxime (Compound 21 in Table I1)

68% yield, NMR d($CDCl_3$) 1.3 (3H, t), 1.91 (2H, m), 2.5 (2H, t), 2.6 (3H, s), 2.78 (2H, t), 4.24 (2H, q), 5.48 (2H, s), 6.73 (1H, dd), 7.05 (1H, d), 7.34 (1H, d); M/z (+) 393 ($MH^+$).

Benzyl 1-(3,4-dichlorobenzyl)-4-oxo-4,5,6,7-tetrahydroindole-2-carboxylate E-O-benzyl Oxime (Compound 22 in Table II)

58% yield, NMR d($CDCl_3$) 1.91 (2H, m), 2.52 (2H, t), 2.72 (2H, t), 5.15 (2H, s), 5.25 (2H, s), 5.5 (2H, s), 6.74 (1H, dd), 7.05 (1H, d), 7.28–7.42 (1H, m); M/z (+) 533 ($MH^+$).

EXAMPLE 16

Ethyl 1-(3,4-dichlorobenzyl)-3-methyl-4oxo-4,5,6,7-tetrahydroindole-2-carboxylate Z-O-ethoxycarbonylbutyl oxime (Compound 23 in Table II)

A solution of ethyl 1-(3,4-dichlorobenzyl)-3-methyl-4-oxo-4,5,6,7-tetrahydroindole-2-carboxylate Z-oxime (0.2 g) in dimethylformamide (2 mL) was added to a suspension of sodium hydride (0.025 g, 60% dispersion in oil) in dimethylformamide (1 mL) and the reaction stirred for 15 minutes. Ethyl-5-bromovalerate (0.15 mL) was added and the reaction stirred at ambient temperature for 18 hours. The reaction was poured into water and extracted with ethyl acetate. Combined organic extracts were dried, concentrated in vacuo and the residue purified by column chromatography using iso-hexane to iso-hexane : 20% ethyl acetate as eluent to give the product as a clear gum (0.25 g, 94%), NMR d($CDCl_3$) 1.25 (3H, t), 1.3 (3H, t), 1.75 (4H, m), 1.88 (2H, m), 2.35 (2H, t), 2.5 (2H, t), 2.62 (3H, s), 2.71 (2H, t), 4.12 (4H, m), 4.25 (2H, q), 5.48 (2H, s), 6.72 (1H, dd), 7.05 (1H, d), 7.35 (1 H, d); M/z (+) 523 ($M^+$).

EXAMPLE 17

The procedure of Example 16 was repeated using the appropriate alkyl halide. Thus were obtained the compounds described below.

Ethyl 1-(3,4-dichlorobenzyl)-3-methyl-4-oxo-4,5.6,7-tetrahydroindole-2-carboxylate Z-O-4'-methoxycarbonylbenzyl oxime (Compound 24 in Table II)

84% yield, NMR d($CDCl_3$) 1.3 (2H, t), 1.9 (2H, m), 2.5 (2H, t), 2.55 (3H, s), 2.75 (2H, t,), 3.91 (3H, s), 4.25 (2H, q), 5.2 (2H, s), 5.48 (2H, s), 6.72 (1H, dd), 7.05 (1H, d), 7.31 (1H, d), 7.48 (2H, d), 8.04 (2H, d); M/z (+) 543 ($M^+$).

Ethyl -(3,4-dichlorobenzyl)-3-methyl-4-oxo-4,5,6,7-tetrahydroindole-2-carboxylate Z-O-3'-methoxycarbonylbenzyl oxime (Compound 25 in Table II)

41% yield, NMR d($CDCl_3$) 1.28 (3H, t), 1.88 (2H, m), 2.5 (2H, t), 2.58 (3H, s), 2.72 (2H, t), 3.92 (3H, s), 4.22 (2H, q), 5.18 (2H, s), 5.45 (2H, s), 6.71 (1H, dd), 7.04 (1H, d), 7.32 (1H, d), 7.44 (1H, dd), 7.62 (1H, dd), 7.98 (1H, dd), 8.1 (1H, dd); M/z (+) 543 ($M^+$).

Ethyl 1-(3,4-dichlorobenzyl)-3-methyl-4-oxo-4,5,6,7-tetrahydroindole-2-carboxylate Z-O-ethoxycarbonylpropyl Oxime (Compound 26 in Table II)

39% yield, NMR d($CDCl_3$) 1.25 (2H, t), 1.3 (2H, t), 1.78 (2H, m), 2.05 (2H, m), 2.45 (2H, t), 2.5 (2H, t), 2.61 (3H, s), 2.7 (2H, t), 4.14 (2H, q), 4.25 (2H, q) 5.48 (2H, s), 6.74 (1H, dd), 7.05 (1H, d), 7.34 (1H, d); M/z (+) 509 ($M^+$).

EXAMPLE 18

The procedure described in Example 3 was repeated using the appropriate 4,5,6,7-tetrahydroindole-2-carboxylate. Thus were obtained the compounds described below.

1-(3,4-Dichlorobenzyl)-3-methyl-4-oxo-4,5,6,7-tetrahydroindole-2-carboxylic acid Z-O-methyl Oxime (Compound 27 in Table II)

48% yield, NMR d(DMSO) 1.75 (2H, m), 2.48 (3H, s), 2.51 (2H, t), 2.56 (2H, t), 3.76 (3H, s), 5.5 (2H, s), 6.84 (1H, dd), 7.22 (1H, d), 7.54 (1H, d); M/z (–) 379 ($M-H^+$).

1-(3,4-Dichlorobenzyl)-3-methyl-4-oxo-4,5,6,7-tetrahydroindole-2-carboxylic acid Z-O-benzyl Oxime (Compound 28 in Table II)

49% yield, NMR d(DMSO) 1.75 (2H, m), 2.48 (3H, s), 2.5 (2H, t), 2.61 (2H, t), 5.05 (2H, s), 5.5 (2H, s), 6.8 (1H, dd), 7.14 (1H, d), 7.15–7.21 (5H, m), 7.52 (1H, d); M/z (–) 455 ($M-H^+$).

1-(3,4-Dichlorobenzyl)-3-meth-4-oxo-4,5,6,7-tetrahydroindole-2-carboxylic acid Z-O-carboxymethyl Oxime (Compound 29 in Table II)

78% yield, NMR d(DMSO) 1.72 (2H, m), 2.41 (3H, s), 2.43 (2H, t), 2.6 (2H, t), 4.41 (2H, s), 5.55 (2H, s), 6.82 (1H, dd), 7.25 (1H, dd), 7.52 (1H, d); M/z (–) 423 ($M-H^+$).

1-(3,4-Dichlorobenzyl)-3-methyl-4-oxo-4,5,6,7-tetrahydroindole-2-carboxylic acid Z-oxime (Compound 30 in Table II)

NMR d(DMSO) 1.72 (2H, m), 2.48 (3H, s), 2.5 (2H, t), 2.55 (2H, t), 5.5 (2H, s), 6.82 (1H, dd), 7.21 (1H, d), 7.53 (1H, d); M/z (–) 365 ($M-H^+$).

1-(3,4-Dichlorobenzyl)-4-oxo-4,5,6,7-tetrahydroindole-2-carboxylic acid Z-O-carboxymethyl Oxime (Compound 31 in Table II)

75% yield, NMR d(DMSO) 1.84 (2H, m), 2.32 (2H, t), 2.6 (2H, t), 4.52 (2H, s), 5.58 (2H, s), 6.85 (1H, dd), 7.28 (1H, d), 7.55 (1H, d), 7.6 (1H, d); M/z (–) 409 ($M-H^+$).

1-(3,4-Dichlorobenzyl)-4oxo-4,5,6,7-tetrahydroindole-2-carboxylic acid E-O-carboxymethyl Oxime (Compound 32 in Table II)

51% yield, NMR d(DMSO) 1.8 (2H, m), 2.53 (2H, t), 2.6 (2H, t), 4.5 (2H, s), 5.54 (2H, s), 6.85 (1H, dd), 6.95 (1H, s), 7.28 (1H, d), 7.55 (1H, d); M/z (–) 409 ($M-H^+$).

1-(3,4-Dichlorobenzyl)-4-oxo-4,5,6,7-tetrahydroindole-2-carboxylic acid E-O-benzyl Oxime (Compound 33 in Table II)

21% yield, NMR d(DMSO) 1.79 (2H, m), 2.52 (2H, t), 2.59 (2H, t), 5.06 (2H, s), 5.52 (2H, s), 6.86, (1H, dd), 6.98 (1H, s), 7.28 (1H, d), 7.3–7.38 (5H, m), 7.56 (1H, d); M/z (–) 441 25 ($M-H^+$).

1-(3,4-Dichlorobenzyl)-3-methyl-4-oxo-4,5,6,7-tetrahydroindole-2-carboxylic Acid Z-O-3'-carboxybenzyl oxime (Compound 34 in Table II)

46% yield, NMR d(DMSO) 1.75 (2H, m), 2.45 (3H, s), 2.61 (2H, t), 2.48 (2H, t), 5.1 30 (2H, s), 5.48 (2H, s), 6.8 (1H, dd), 7.24 (1H, d), 7.45 (1H, dd), 7.52 (1H, d), 7.62 (1H, dd), 7.85 (1H, dd), 7.95 (1H, bs); M/z (–) 499 ($M-H^+$).

1-(3,4-Dichlorobenzyl)-3-methyl-4-oxo-4,5,6,7-tetrahydroindole-2-carboxylic Acid Z-O-carboxypropyl Oxime (Compound 35 in Table II)

72% yield, NMR d(DMSO) 1.72 (2H, m), 1.85 (2H, m), 2.26 (2H, t), 2.48 (3H, s), 2.51 (2H, t), 2.55 (2H, t), 4.0 (2H, t), 5.5 (2H, s), 6.8 (1H, dd), 7.24 (1H, d), 7.55 (1H, d); M/z (–) 451 ($M-H^+$).

1-(3,4-Dichlorobenzyl)-3-methyl-4-oxo-4,5,6,7-tetrahydroindole-2-carboxylic acid Z-O-4'-carboxybenzyl Oxime (Compound 36 in Table II)

70% yield, NMR d(DMSO) 1.74 (2H, m), 2.4 (3H, s), 2.51 (2H, t), 2.65 (2H, t), 5.11 (2H, s), 5.51 (2H, s), 6.8 (1H, dd), 7.24 (1H, d), 7.46 (2H, d), 7.51 (1H, d), 7.9 (2H, d), 12.56 (2H, s); M/z (–) 499 ($M-H^+$).

1-(3,4-Dichlorobenzyl)-3-methyl-4-oxo-4,5,6,7-tetrahydroindole-2-carboxylic acid Z-O-carboxybutyl Oxime (Compound 37 in Table II)

55% yield, NMR d(DMSO) 1.5–1.68 (4H, m), 1.75 (2H, m), 2.22 (2H, t), 2.48 (3H, s), 2.50 (2H, t), 2.58 (2H, t), 4.0 (2H, t), 5.5 (211, s), 6.82 (1H, dd), 7.22 (1H, d), 7.52 (1H, d); M/z (–) 465 ($M-H^+$).

EXAMPLE 19

Biological Assays for hMCP-1 Antagonists a) hMCP-1 Receptor-binding Assay i) Cloning and Expression of hMCP-1 Receptor The MCP-1 receptor B (CCR2B) cDNA was cloned by PCR from THP-1 cell RNA using suitable oligonucleotide primers based on the published MCP-1 receptor sequences (Charo et al., 1994, *Proc. Natl. Acad. Sci. USA,* 91, 2752).

The resulting PCR products were cloned into vector PCR-II™ (InVitrogen, San Diego, Calif.). Error free CCR2B cDNA was subcloned as a Hind III-Not I fragment into the eukaryotic expression vector pCDNA3 (InVitrogen) to generate pCDNA3/CC-CKR2A and pCDNA3/CCR2B respectively.

Linearised pCDNA3/CCR2B DNA was transfected into CHO-KI cells by calcium phosphate precipitation (Wigler et al., 1979, *Cell,* 16, 777). Transfected cells were selected by the addition of Geneticin Sulphate (G418, Gibco BRL) at 1 mg/ml, 24 hours after the cells had been transfected. Preparation of RNA and Northern blotting were carried out as described previously (Needham et al., 1995, *Prot. Express. Purific.,* 6, 134). CHO-K1 clone 7 (CHO-CCR2B) was identified as the highest MCP-1 receptor B expressor.

ii) Preparation of Membrane Fragments

CHO-CCR2B cells were grown in DMEM supplemented with 10% foetal calf serum, 2 mM glutamine, lx Non-Essential Amino Acids, 1× Hypoxanthine and Thymidine Supplement and Penicillin-Streptomycin (at 50 $\mu$g streptomycin/ml; Gibco BRL). Membrane fragments were prepared using cell lysis/differential centrifugation methods as described previously (Siciliano et al., 1990, *J. Biol. Chem.,* 265, 19658). Protein concentration was estimated by BCA protein assay (Pierce, Rockford, Ill.) according to the manufacturer's instructions, iii) Assay $^{125}$I MCP-1 was prepared using Bolton and Hunter conjugation (Bolton et al., 1973, *Biochem. J.,* 133, 529; Amersham International plc]. Equilibrium binding assays were carried out using the method of Ernst et al., 1994, *J Immunol.,* 152, 3541. Briefly, varying amounts of $^{125}$I-labeled MCP-1 were added to 10 mg of purified CHO-CCR2B cell membranes in 100 ml of Binding Buffer. After I hour incubation at room temperature the binding reaction mixtures were filtered and washed 5 times through a plate washer (Packard Harvester Filtermate™ 196). Scintillation fluid (25 $\mu$l, Microscint™-20, a high efficiency liquid scintillation counting cocktail for aqueous samples) was added to each well and the plate was covered with plate sealer and counted (Packard Top Count™). Cold competition studies were performed as above using 100 pM $^{125}$I-labeled MCP-1 in the presence of varying concentrations of unlabelled MCP-1. Non-specific binding was determined by the inclusion of a 200-fold molar excess of unlabelled MCP-1 in the reaction.

Ligand binding studies with membrane fragments prepared from CHO-CCR2B cells showed that the CCR2B was present at a concentration of 0.2 pmoles/mg of membrane protein and bound MCP-1 selectively and with high affinity ($IC_{50}$=110 pM, $K_d$=120 pM). Binding to these membranes was completely reversible and reached equilibrium after 45 minutes at room temperature, and there was a linear relationship between MCP-1 binding and CHO-CCR2B cell membrane concentration when using MCP-1 at concentrations between 100 pM and 500 pM.

Test compounds dissolved in DMSO (5 $\mu$l) were tested in competition with 100 pM labelled MCP-1 over a concentration range (0.1–200 $\mu$M) in duplicate using eight point dose-response curves and $IC_{50}$ concentrations were calculated.

Compounds tested of the present invention had $IC_{50}$ values of less than 5 $\mu$M in the hMCP-1 receptor binding assay described herein. For example the compound of example 4a had an $IC_{50}$ of 0.4 $\mu$M.

b) MCP-1 Mediated Calcium Flux in THP-1 Cells

The human monocytic cell line THP-1 was grown in a synthetic cell culture medium RPMI 1640 supplemented with 10% foetal calf serum, 2 mM glutamine and Penicillin-Streptomycin (at 50 $\mu$g streptomycin/ml, Gibco BRL). THP-1 cells were washed in HBSS (lacking $Ca^{2+}$ and $Mg^{2+}$)+1 mg/ml BSA and resuspended in the same buffer at a density of 3×10$^6$ cells/ml. The cells were then loaded with 1 mM FURA-2/AM for 30 min at 37° C., washed twice in HBSS, and resuspended at 1×10$^6$ cells/ml. THP-1 cell suspension (0.9 ml) was added to a 5 ml disposable cuvette containing a magnetic stirrer bar and 2.1 ml of prewarmed (37° C.) HBSS containing 1 mg/ml BSA, 1 mM $MgCl_2$ and 2 mM $CaCl_2$. The cuvette was placed in a fluorescence spectrophotometer (Perkin Elmer, Norwalk, Conn.) and pre-incubated for 4 min at 37° C. with stirring. Fluorescence was recorded over 70 sec and cells were stimulated by addition of hMCP-1 to the cuvette after 10 sec. [$Ca^{2+}$]i was measured by excitation at 340 nm and 380 nm alternately and subsequent measurement of the intensity of the fluorescence emission at 510 nm. The ratio of the intensities of the emitted fluorescent light following excitation at 340 nm and 380 nm, (R), was calculated and displayed to give and estimate of cytoplasmic [$Ca^{2+}$] according to the equation:

$$[Ca^{2+}]i = K_d \frac{(R - Rmin)}{(Rmax - R)} (Sf2/Sb2)$$

where the $K_d$ for FURA-2 $Ca^{2+}$ complex at 37° C. was taken to be 224 nm. $R_{max}$ is the maximal fluorescence ratio determined after addition of 10 mM lonomycin, $R_{min}$ is the minimal ratio determined by the subsequent addition of a $Ca^{2+}$ free solution containing 5 mM EGTA, and Sf2/Sb2 is the ratio of fluorescence values at 380 nm excitation determined at $R_{min}$ and $R_{max}$, respectively.

Stimulation of THP-1 cells with hMCP-1 induced a rapid, transient rise in [$Ca^{2+}$]i in a specific and dose dependent manner. Dose response curves indicated an approximate $EC_{50}$ of 2 nm. Test compounds dissolved in DMSO (10 $\mu$l) were assayed for inhibition of calcium release by adding them to the cell suspension 10 sec prior to ligand addition and measuring the reduction in the transient rise in [$Ca^{2+}$]i. Test compounds were also checked for lack of agonism by addition in place of hMCP-1.

c) hMCP-1 Mediated Chemotaxis and RANTES Assay.

In vitro chemotaxis assays were performed using either the human monocytic cell line THP-1 or peripheral blood mixed monocytes obtained from fresh human blood purified by erythrocyte sedimentation followed by density gradient centrifugation over 9.6%(w/v) sodium metrizoate and 5.6% (w/v) polysaccharide, density 1.077 g/ml (Lymphoprep™ Nycomed). Cell migration through polycarbonate membranes was measured by enumerating those passing through either directly by Coulter counting or indirectly by use of a colourimetric viability assay measuring the cleavage of a tetrazolium salt by the mitochondrial respiratory chain (Scudiero D. A. et al. 1988, *Cancer Res.,* 48, 4827–4833).

Chemoattractants were introduced into a 96-well microtiter plate which forms the lower well of a chemotaxis chamber fitted with a PVP-free 5 $\mu$m poresize polycarbonate adhesive framed filter membrane (NeuroProbe MB series, Cabin John, Md. 20818, USA) according to the manufacturer's instructions. The chemoattractant was diluted as appropriate in synthetic cell culture medium, RPMI 1640 (Gibco) or supplemented with 2 mM glutamine and 0.5% BSA, or alternatively with HBSS with Ca2+ and Mg2+ without Phenol Red (Gibco) plus 0.1% BSA. Each dilution was degassed under vacuum for 30 min and was placed (400 $\mu$l) in the lower wells of the chamber and THP-1 cells (5×10$^5$ in 100 $\mu$l RPMI 1640+0.5%BSA) were incubated in each well of the upper chamber. For the inhibition of chemotaxis the chemoattractant was kept at a constant submaximal concentration determined previously for each chemokine (1 nM for MCP-1 and 2 nM for RANTES) and added to the lower well together with the test compounds dissolved in DMSO (final DMSO concentration <0.05% v/v) at varying concentrations. The chamber was incubated for 2 h at 37° C. under 5 % $CO_2$. The medium was removed from the upper wells which were then washed out with 200 μl physiological saline before opening the chamber, wiping dry the membrane surface and centrifuging the 96-well plate at 600 g for 5 min to harvest the cells. Supernatant (150 μl) was aspirated and 10 μl of cell proliferation reagent, WST-1, {4-[3-(4-iodophenyl)-2-(4-nitrophenyl)-2H-5-tetrazolio]-1,3-phenyl disulfonate} plus an electron coupling reagent (Bochringer Marnnheim, Cat.no. 1644 807) was added back to the wells. The plate was incubated at 37° C. for 3 h and the absorbance of the soluble formazan product was read on a microtitre plate reader at 450 mn. The data was input into a spreadsheet, corrected for any random migration in the absence of chemoattractant and the average absorbance values, standard error of the mean, and significance tests were calculated. hMCP-1 induced concentration dependent cell migration with a characteristic biphasic response, maximal 0.5–1.0 nm.

In an alternative form of the above assay, fluorescently tagged cells can be used in order to assist in end point detection. In this case, the THP-1 cells used are fluorescently tagged by incubation in the presence of 5 mM Calcein AM (Glycine, N,N'-[[3',6'-bis(acetyloxy)-3-oxospiro [isobenzofuran-1(3H),9'-[9H]xanthene]-2',7'-diyl]bis (methylene)]bis[N-[2-[(acetyloxy)methoxy]-2-oxoethyl]]-bis[(acetyloxy)methyl] ester; Molecular Probes) for 45 minutes in the dark. Cells are harvested by centrifugation and resuspended in HBSS (without Phenol Red) with Ca2+, Mg2+and 0.1% BSA. 50 ml (2×105 cells) of the cell suspension are placed on the filter above each well and, as above, the unit is incubated at 37° C. for 2 hours under 5% $CO_2$. At the end of the incubation, cells are washed off the upper face of the filter with phosphate buffered saline, the filter removed from the plate and the number of cells attracted to either the underside of the filter or the lower well estimated by reading fluorescence at 485 nm excitation, 538 nm emission wavelengths (fmax, Molecular Devices). The data was input into a spreadsheet, corrected for any random migration in the absence of chemoattractant and the average fluorescence values, standard error of the mean, percentage inhibition and IC50 of compounds under test and significance tests can be calculated.

No physiologically unacceptable toxicity was observed at the effective dose for compounds tested of the present invention.

EXAMPLE 19

Pharmaceutical Compositions

The following Example illustrates, but is not intended to limit, pharmaceutical dosage forms of the invention as defined herein (the active ingredient being termed "Compound X"), for therapeutic or prophylactic use in humans:

| (a)<br>Tablet I | mg/tablet |
|---|---|
| Compound X. | 100 |
| Lactose Ph.Eur | 182.75 |
| Croscarmellose sodium | 12.0 |
| Maize starch paste (5% w/v paste) | 2.25 |
| Magnesium stearate | 3.0 |

-continued

| (b)<br>Tablet II | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c)<br>Tablet III | mg tablet |
|---|---|
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d)<br>Capsule | mg capsule |
|---|---|
| Compound X | 10 |
| Lactose Ph.Eur | 488.5 |
| Magnesium | 1.5 |

| (e)<br>Injection I | (50 mg/ml) |
|---|---|
| Compound X | 5.0% w/v |
| 1M Sodium hydroxide solution | 15.0% v/v |
| 0.1M Hydrochloric acid | to adjust pH to 7.6 |
| Polyethylene glycol 400 | 4.5% w/v |
| Water for injection | to 100% |

| (f)<br>Injection II | (10 mg/ml) |
|---|---|
| Compound X | 1.0% w/v |
| Sodium phosphate BP | 3.6% w/v |
| 0.1M Sodium hydroxide solution | 15.0% v/v |
| Water for injection | to 100% |

| (g)<br>Injection III | (1 mg/ml. buffered to pH6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection | to 100% |

| (h)<br>Aerosol I | mg/ml |
|---|---|
| Compound X | 10.0 |
| Sorbitan trioleate | 13.5 |
| Trichlorofluoromethane | 910.0 |
| Dichlorodifluoromethane | 490.0 |

| (i)<br>Aerosol II | mg/ml |
|---|---|
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |

| (j)<br>Aerosol III | mg/ml |
|---|---|
| Compound X | 2.5 |
| Sorbitan trioleate | 3.38 |
| Trichlorofluoromethane | 67.5 |

-continued

| | |
|---|---|
| Dichlorodifluoromethane | 1086.0 |
| Dichlorotetrafluoroethane | 191.6 |
| (k) Aerosol IV | mg/ml |
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |
| (l) Ointment | ml |
| Compound X | 40 mg |
| Ethanol | 300 μl |
| Water | 300 μl |
| 1-Dodecylazacycloheptan-2-one | 50 μl |
| Propylene glycol | to 1 ml |

Note:

Compound X in the above formulation may comprise a compound illustrated in Examples 1 to 18 herein, for Example, the compounds of Examples 3, 4, 5, 13 and 18. The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

What is claimed is:

1. A pharmaceutical composition which comprises a compound of formula (I)

(I)

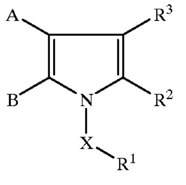

or a pharmaceutically acceptable salt, ester or amide thereof, which is an inhibitor of monocyte chemoattractant protein-1, and wherein A and B form an optionally substituted alkylene chain so as to form a ring with the carbon atoms to which they are attached;

X is $CH_2$ or $SO_2$ $R^1$ is an optionally substituted aryl or heteroaryl ring;

$R^2$ is carboxy, cyano, —C(O)$CH_2$OH, —CONH$R^4$, —$SO_2$NH$R^5$, tetrazol-5-yl, $SO_3$H, or a group of formula (VI)

(VI)

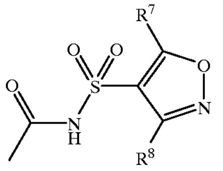

where $R^4$ is selected from hydrogen, alkyl, aryl, cyano, hydroxy, —$SO_2R^9$ where $R^9$ is alkyl, aryl, heteroaryl, or haloalkyl, or $R^4$ is a group-$(CHR^{10})_r$—COOH where r is an integer of 1–3 and each $R^{10}$ group is independently selected from hydrogen or alkyl; $R^5$ is hydrogen, alkyl, optionally substituted aryl or optionally subtituted heteroaryl, or a group $COR^6$ where $R^6$ is hydrogen, alkyl, aryl, heteroaryl or haloalkyl; $R^1$ and $R^8$ are independently selected from hydrogen or alkyl, particularly $C_{1-4}$alkyl; and $R^3$ is hydrogen, a functional group, optionally substituted alkyl, optionally substituted alkenyl, optionally substituted alkynyl, optionally substituted aryl, optionally substituted heterocyclyl, optionally substituted alkoxy, optionally substituted aralkyl, optionally substituted aralkyloxy, optionally substituted cycloalkyl; in combination with a pharmaceutically acceptable carrier.

2. The composition according to claim 1 wherein the compound of formula (I) is a compound of formula (III)

(III)

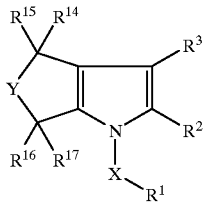

wherein $R^1$, $R^2$, $R^3$ and X are as defined in claim 1, Y is a group $(CR^{18}R^{19})_s$, $R^{14}$, $R^{15}$, $R^{16}$, $R^{17}$ and each $R^{18}$ and $R^{19}$, are independently selected from hydrogen, alkyl, cycloalkyl, alkenyl, cycloalkenyl, alkynyl, cycloalkynyl or a functional group, and s is an integer of from 1 to 4.

3. The composition according to claim 2 wherein in the compound of formula (I), $R^{14}$, $R^{15}$, $R^{16}$, $R^{17}$ and each $R^{18}$ and $R^{19}$ are independently selected from hydrogen; trifluoromethyl; $C_{1-4}$alkyl which is optionally substituted by aryl, carboxy or amide derivatives thereof; halo;

hydroxy; $C_{1-4}$alkoxy; $C_{1-4}$alkanoyl; $C_{1-4}$alkanoyloxy; amino; cyano; $C_{1-4}$alkylamino; di($C_{1-4}$alkyl)amino; $C_{1-4}$alkanoylamino; nitro; carbarnoyl; $C_{1-4}$alkoxycarbonyl; thiol; $C_{1-4}$alkylsulphanyl; $C_{1-4}$alkylsulphinyl; $C_1$4alkylsulphonyl; sulphonamido; alkylsulphonamido, arylsulphonamido, carbamoyl$C_{1-4}$alkyl; N-($C_{1-4}$alkyl)carbamoyl$C_{1-4}$alkyl; N-($C_{1-4}$alkyl)$_2$carbamoyl-$C_{1-4}$alkyl; hydroxy$C_{1-4}$alkyl; $C_{1-4}$alkoxy$C_{1-4}$alkyl; morpholino; thiomorpholino; oxythiomorpholino; pyrrolidinyl; carboxy$C_{1-4}$alkylamino; $R^{20}$; NH$R^{21}$ and —O$R^{21}$ where $R^{20}$ and $R^{21}$ are independently selected from optionally substituted phenyl or an optionally substituted 5- or 6-membered heteroaryl ring; Or $R^{14}$ and $R^{15}$, $R^{16}$ and $R^{17}$, and/or $R^{18}$ and $R^{19}$ together form an oxo group or a group =NO$R^{22}$ where $R^{22}$ is hydrogen or an optionally substituted hydrocarbyl group; with the proviso that $R^{14}$ and $R^{15}$, or $R^{16}$ and $R^{17}$ or $R^{18}$ and the $R^{19}$ which is attached to the same carbon atom, are not both hydroxy, $C_{1-4}$alkoxy, amino, cyano, nitro or thiol.

4. The composition according to any one of claims 1 to 3 where X is $CH_2$.

5. The composition according to any one of claims 1 to 3 where $R^1$ is an optionally substituted phenyl, naphthyl, furyl or thienyl ring.

6. The composition according to any one of claims 1 to 3 where $R^2$ is carboxy or a pharmaceutically acceptable salt or ester thereof.

7. The composition according to claim 2 wherein the compound of formula (I) comprises a compound of formula (III) where $R^2$ is carboxy, X and $R^1$ are as defined in claim 1, $R^3$ is hydrogen or $C_{1-4}$ alkyl, s is as defined in claim 2, $R^{14}$ and $R^{15}$ are selected from hydrogen, =O, =NOH, =NOR* where R* is methyl, benzyl, carboxybenzyl, methoxycarbonylbenzyl, 3-(carboxy)propyl or an ester thereof such as the ethyl ester, 4-carboxybutyl or an ester thereof and carboxymethyl, and $R^{16}$, $R^{17}$, $R^{18}$ and $R^{19}$ are all hydrogen; or a pharmaceutically acceptable salt or an in vivo hydrolysable ester thereof.

8. A method of preparing a compound according to claim 9 which method comprises reacting a compound of formula (VII)

VII

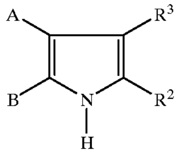

where A, B, $R^2$ and $R^3$ are as defined in claim 1; with compound of formula (VIII)

$R^1$-X-Z VIII where $R^1$ and X are as defined in claim 1 and Z is a leaving group; and optionally thereafter carrying out one or more of the following steps:

(i) converting the group $R^2$ to a different such group:

(ii) introducing or changing a substitutent on the groups A–B:

(iii) converting the group $R^3$ to a different such group.

9. A compound of formula (I)

(I)

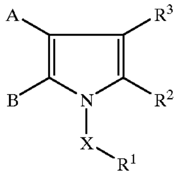

or a pharmaceutically acceptable salt, ester or amide thereof, wherein:

A and B form an optionally substituted alkylene chain so as to form a ring with the carbon atoms to which they are attached;

X is $CH_2$ or $SO_2$;

$R^1$ is an optionally substituted aryl or heteroaryl ring;

$R^2$ is carboxy, cyano, —C(O)$CH_2$OH, —CONHR$^4$, —$SO_2$NHR$^5$, tetrazol-5-yl, $SO_3$H, or a group of formula (VI)

(VI)

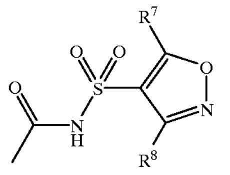

where $R^4$ is selected from hydrogen, alkyl, aryl, cyano, hydroxy, —$SO_2R_9$ where $R^9$ is alkyl, aryl, heteroaryl, or haloalkyl, or $R^4$ is a group-$(CHR^{10})_r$—COOH where r is an integer of 1–3 and each $R^{10}$ group is independently selected from hydrogen or alkyl; $R^5$ is hydrogen, alkyl, optionally substituted aryl or optionally substituted heteroaryl, or a group COR$^6$ where $R^6$ is hydrogen, alkyl, aryl, heteroaryl or haloalkyl; $R^7$ and $R^8$ are independently selected from hydrogen or alkyl, particularly $C_{1-4}$ alkyl; and $R^3$ is hydrogen, a functional group, optionally substituted alkyl, optionally substituted alkenyl, optionally substituted alkynyl, optionally substituted aryl, optionally substituted heterocyclyl, optionally substituted alkoxy, optionally substituted aralkyl, optionally substituted aralkyloxy, optionally substituted cycloalkyl;

provided that where A and B form —$(CH_2)_3$—, X is $CH_2$, $R^2$ is carboxy or an ester or amide thereof, and $R^3$ is hydrogen, $R^1$ is other than unsubstituted phenyl.

10. The compound according to claim 9 wherein the compound of formula (I) is a compound of formula (III):

(III)

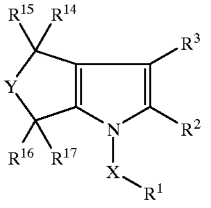

wherein $R^1$, $R^2$, $R^3$ and X are as defined in claim 11, Y is a group $(CR^{18}R^{19})_s$, $R^{14}$, $R^{15}$, $R^{16}$, $R^{17}$ and each $R^{18}$ and $R^{19}$, are independently selected from hydrogen, alkyl, cycloalkyl, alkenyl, cycloalkenyl, alkynyl, cycloalkynyl or a functional group, and s is an integer of from 1 to 4.

11. The compound according to claim 10 wherein $R^{14}$, $R^5$, $R^{16}$, $R^{17}$ and each $R^{18}$ and $R^{19}$ are independently selected from hydrogen; trifluoromethyl; $C_{1-4}$alkyl which is optionally substituted by aryl, carboxy or amide derivatives thereof; halo; hydroxy; $C_{1-4}$alkoxy; $C_{1-4}$alkanoyl; $C_{1-4}$alkanoyloxy; amino; cyano; $C_{1-4}$alkylamino; di($C_{1-4}$alkyl)amino; $C_{1-4}$alkanoylamino; nitro; carbamoyl; $C_{1-4}$alkoxycarbonyl; thiol; $C_{1-4}$alkylsulphanyl; $C_{1-4}$alkylsulphinyl; $C_{1-4}$alkylsulphonyl; sulphonamido; alkylsulphonamido, arylsulphonamido, carbamoyl$C_{1-4}$alkyl; N-($C_{1-4}$alkyl)carbamoyl$C_{1-4}$alkyl; N-$(C_{1-4}alkyl)_2$carbamoyl-$C_{1-4}$alkyl; hydroxy$C_{1-4}$alkyl; $C_{1-4}$alkoxy$C_{1-4}$alkyl; morpholino; thiomorpholino; oxythiomolpholino; pyrTolidinyl; carboxy$C_{1-4}$alkylamino; $R^{20}$; NHR$^{21}$ and —OR$^{21}$ where $R^{20}$ and $R^{21}$ are independently selected from optionally substituted phenyl or an optionally substituted 5- or 6-membered heteroaryl ring; or $R^{14}$ and $R^{15}$, $R^{16}$ and $R^{17}$, and/or $R^{18}$ and $R^{19}$ together form an oxo group or a group =NOR$^{22}$ where $R^{22}$ is hydrogen or an optionally substituted hydrocarbyl group; with the proviso that $R^{14}$ and $R^{15}$, or $R^{10}$ and $R^{17}$ or $R^{18}$ and the $R^{19}$ which is attached to the same carbon atom, are not both hydroxy, $C_{1-4}$alkoxy, amino, cyano, nitro or thiol.

12. The compound according to any one of claims 9 to 11 where X is $CH_2$.

13. The compound according to any one of claims 9 to 11 where $R^1$ is an optionally substituted phenyl, naphthyl, furyl or thienyl ring.

14. The compound according to any one of claims 9 to 11 where $R^2$ is carboxy or a pharmaceutically acceptable salt or ester thereof.

15. The compound according to claim 10 wherein $R^2$ is carboxy, X is $CH_2$ or $SO_2$ and $R^1$ is an optionally substituted aryl or heteroaryl ring, $R^3$ is hydrogen or $C_{1-4}$ alkyl, s is as defined in claim 10, $R^{14}$ and $R^{15}$ are selected from hydrogen, $=O$, $=NOH$, $=NOR^{11}$ where R* is methyl, benzyl, carboxybenzyl, methoxycarbonylbenzyl, 3-(carboxy)propyl or an ester thereof, 4-carboxybutyl or an ester thereof, and carboxymethyl, and $R^{16}$, $R^{17}$, $R^{18}$ and $R^{19}$ are all hydrogen; or a pharmaceutically acceptable salt or an in vivo hydrolysable ester thereof.

16. A method for treating an inflammatory disease in a warm blooded animal in need there of, which comprises administering to said animal an effective amount of a composition according to claim 1, or a pharmaceutically acceptable salt, or an in vivo hydrolysable ester thereof.

17. A method for antagonising an MCP-1 mediated effect in a warm blooded animal in need thereof, which comprises administering to said animal an effective amount of a composition according to claim 1, or a pharmaceutically acceptable salt, or an in vivo hydrolysable ester thereof.

* * * * *

UNITED STATES PATENT AND TRADEMARK OFFICE

CERTIFICATE OF CORRECTION

PATENT NO. : 6,291,507 B1
DATED : September 18, 2001
INVENTOR(S) : Faull et al.

It is certified that error appears in the above-identified patent and that said Letters Patent is hereby corrected as shown below:

Title page,
Please change Item [22] to read:
-- [22] PCT Filed: 2 Feb. 1999 --.

Please insert the following lines following Item [22]:
-- [86] PCT No.: PCT/GB99/00332
§ 371 Date: 26 Jul. 2000
§ 102(e) Date: 26 Jul 2000

[87] PCT Pub. No.: WO 99/40913
PCT Pub. Date: 19 Aug. 1999 --

Column 1,
After the title and before the first paragraph, please insert as a separate paragraph:
-- This application in the National Phase of International Application PCT/GB99/00332 filed February 2, 1999 which designated the U.S. --.

Signed and Sealed this

Sixteenth Day of April, 2002

Attest:

JAMES E. ROGAN
*Director of the United States Patent and Trademark Office*

*Attesting Officer*